(12) United States Patent
Lennox

(10) Patent No.: US 7,156,867 B2
(45) Date of Patent: Jan. 2, 2007

(54) UNIFORM SELECTIVE CEREBRAL HYPOTHERMIA

(75) Inventor: Charles D. Lennox, Hudson, NH (US)

(73) Assignee: MedCool, Inc., Westwood, MA (US)

( * ) Notice: Subject to any disclaimer, the term of this patent is extended or adjusted under 35 U.S.C. 154(b) by 565 days.

(21) Appl. No.: 10/330,638

(22) Filed: Dec. 27, 2002

(65) Prior Publication Data

US 2003/0130651 A1 Jul. 10, 2003

Related U.S. Application Data

(60) Provisional application No. 60/344,986, filed on Dec. 31, 2001.

(51) Int. Cl.
*A61F 7/00* (2006.01)
(52) U.S. Cl. ............. 607/105; 607/109; 607/113
(58) Field of Classification Search ........ 607/104–106, 607/113; 604/113, 512
See application file for complete search history.

(56) References Cited

U.S. PATENT DOCUMENTS

| | | | | |
|---|---|---|---|---|
| 4,904,237 A | | 2/1990 | Janese | 604/28 |
| 5,342,301 A | | 8/1994 | Saab | 604/96 |
| 5,486,208 A | | 1/1996 | Ginsburg | 607/106 |
| 5,971,979 A | | 10/1999 | Joye et al. | 606/21 |
| 6,030,412 A | * | 2/2000 | Klatz et al. | 607/104 |
| 6,156,059 A | * | 12/2000 | Olofsson | 607/109 |
| 6,217,552 B1 | | 4/2001 | Barbut et al. | 604/113 |
| 6,312,453 B1 | * | 11/2001 | Stefanile et al. | 607/109 |
| 6,623,514 B1 | | 9/2003 | Chin | 607/105 |
| 6,648,878 B1 | | 11/2003 | Lafontaine | 606/21 |
| 6,660,026 B1 | | 12/2003 | Larnard et al. | 607/104 |
| 6,682,508 B1 | | 1/2004 | Meythaler et al. | 604/246 |
| 6,692,519 B1 | | 2/2004 | Hayes, Jr. | 607/105 |
| 6,699,269 B1 | | 3/2004 | Khanna | 607/105 |
| 6,923,826 B1 | * | 8/2005 | Larnard et al. | 607/105 |
| 2002/0022823 A1 | * | 2/2002 | Luo et al. | 604/512 |
| 2002/0032430 A1 | * | 3/2002 | Luo et al. | 604/512 |

(Continued)

OTHER PUBLICATIONS

Piepgras, et al., "Rapid Active Internal Core Cooling for Induction of Moderate Hypothermia in Head Injury by Use of an Extracorporeal Heat Exchanger", Neurosurgery Online, Feb. 1998, vol. 42, No. 2. http://www.neurosurgery-online.com. Visited Nov. 24, 2003.

(Continued)

*Primary Examiner*—Roy D. Gibson
(74) *Attorney, Agent, or Firm*—Thomas J. Engellenner; Charlton Shen; Nutter McClennen & Fish LLP

(57) ABSTRACT

Disclosed is an apparatus and method for uniform selective cerebral hypothermia. The apparatus includes a brain-cooling probe, a head-cooling cap, a body-heating device and a control console. The brain-cooling probe cools the cerebrospinal fluid within one or more brain ventricles. The brain-cooling probe withdraws a small amount of cerebrospinal fluid from a ventricle into a cooling chamber located ex-vivo in close proximity to the head. After the cerebrospinal fluid is cooled it is then reintroduced back into the ventricle. This process is repeated in a cyclical or continuous manner. The head-cooling cap cools the cranium and therefore cools surface of the brain. The combination of ventricle cooling and cranium cooling provides for whole brain cooling while minimizing temperature gradients within the brain. The body-heating device replaces heat removed from the body by the brain-cooling probe and the head-cooling cap and provides for a temperature difference between the brain and the body where the brain is maintained a temperature lower than the temperature of the body.

39 Claims, 15 Drawing Sheets

U.S. PATENT DOCUMENTS

2002/0198579 A1   12/2002   Khanna ...................... 607/105
2003/0163181 A1*   8/2003   Frazer et al. ............... 607/105

OTHER PUBLICATIONS

Alsius, A New Degree of Care, The Fortius Catheter, http://www.alsius.com/us/fortius.htm. Visited Nov. 24, 2003.

Hachimi-Idrissi, et al., "Mild Hypothermia Induced by a Helmet Device: A Clinical Feasibility Study", Resuscitation 51:275 (2001).

Ommaya, et al., "Direct Extravascular Brain Cooling in the Normothermic Animal", Neurology 12:882 (1962).

Tooley, et al., "Significant Selective Head Cooling can be Maintained Long-Term After Global Hypoxia Ischemia in Newborn Piglets", Pediatrics, vol. 109, No. 4, pp. 643-649, Apr. 2002.

Javid, et al., "Hypothermic Ventricular Perfusion: Evaluation of Use in Cerebrovascular Occlusion, New York State Journal of Medicine", pp. 248-251, Jan. 5, 1967.

Tooley, et al., "Head Cooling with Mild Systemic Hypothermia in Anesthetized Piglets is Neuroprotective", Annals of Neurology, vol. 53, No. 1, pp. 65-72, Jan. 2002.

White, M.D., "Cerebral Hypothermia and Circulatory Arrest: Review and Commentary", Mayo Clin. Proc. 53:450 (1978).

Costal, et al., "Experimental Production of Cerebral Hypothermia by Ventricular Perfusion Techniques", J. Neurosurg, 20:112 (1963).

* cited by examiner

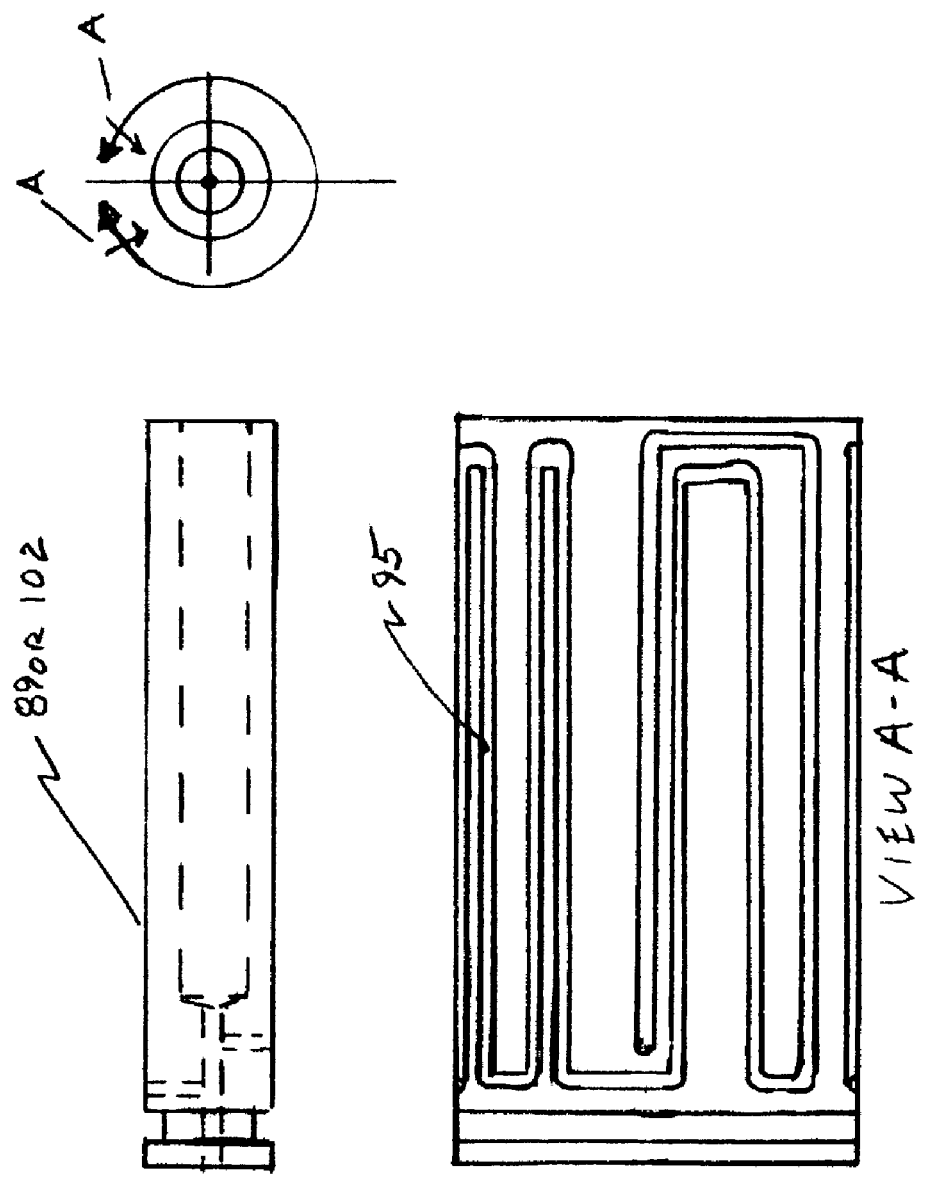

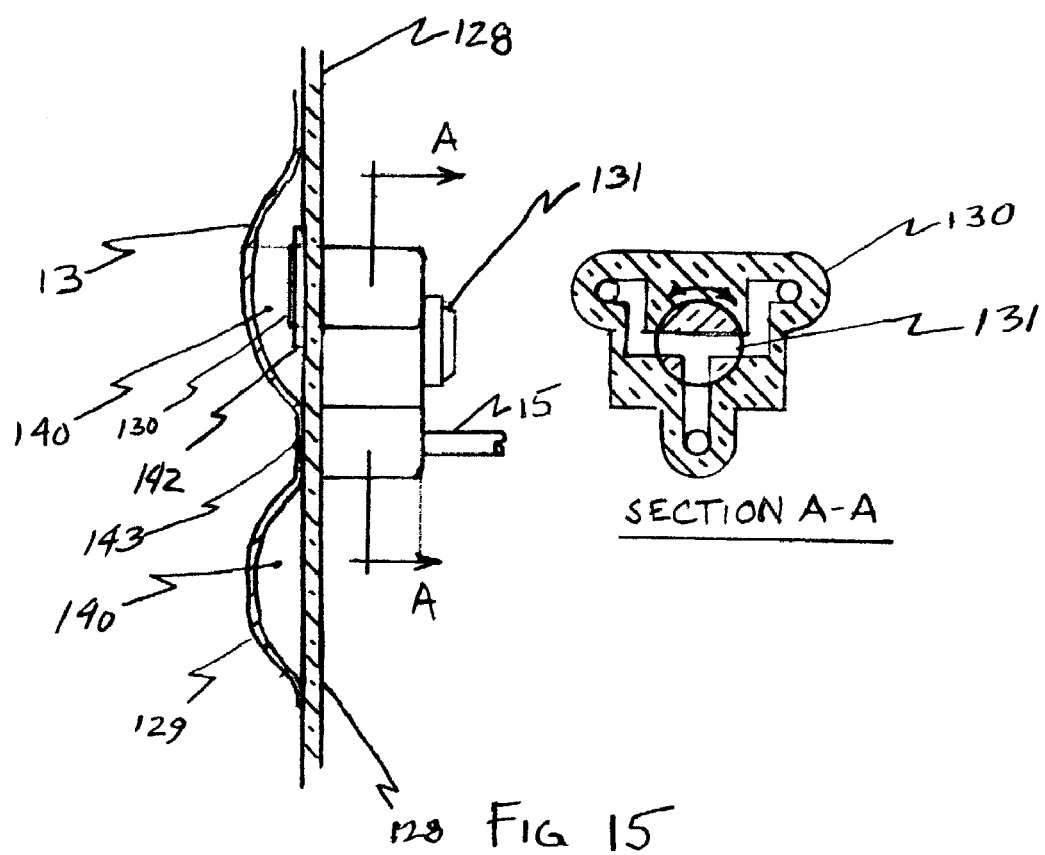

UNIFORM SELECTIVE CEREBRAL HYPOTHERMIA

CROSS REFERENCE TO RELATED APPLICATIONS

This application is entitled to the benefit of Provisional Patent Application Ser. No. 60/344,986 filed Dec. 31, 2001.

BACKGROUND

1. Field of Invention

This invention relates to a method, device and system for inducing global cerebral hypothermia while maintaining normal body core temperature for the prevention of secondary brain injury from stroke, trauma, or surgery.

2. Description of Prior Art

Patients suffering from stroke or head trauma, or have undergone invasive brain or vascular surgery are at risk from secondary brain injury. Secondary brain injury is a result of the innate healing response of the brain to the original insult caused by several not completely understood mechanisms. Regardless of the specific mechanisms involved, the end result is swelling of the brain caused by edema, which can lead to a critical or terminal rise in intra-cranial pressure.

It has long been known that hypothermia is neuroprotective. Hypothermia has a positive affect on all known mechanisms that lead to secondary brain injury. Hypothermia is routinely used during brain and other invasive surgeries to protect the brain from surgical interruptions in blood flow. Hypothermia has also been shown to be effective in controlling swelling of the brain in trauma and stroke patients.

The effectiveness of hypothermia is a function of depth and duration; the deeper the hypothermia, and/or the longer it is applied the more neuroprotective it is. However, hypothermia has historically been applied systemically, and the depth and duration of hypothermia is limited by the patient's ability to tolerate the therapy.

Systemic hypothermia has historically been accomplished by immersion of the patient's body in a cool bath. Today there are several commercial systemic hypothermia systems available. They consist of blankets or pads where cooled water is circulated through channels in the walls of the blanket or pad, and the patient's body is maintained in intimate contact. Medivan Corp. manufactures an example of a modern hypothermia system under the trade name Arctic Sun Cooling System.

Systemic hypothermia has been demonstrated to be effective in reducing secondary injury from stroke, trauma, and surgery however, there are several drawbacks to this approach: 1) It takes several hours to lower a patient's body to therapeutic temperatures. This delay in achieving therapeutic temperatures allows for the progression of irreversible secondary injury to the brain. 2) The practical therapeutic hypothermic temperature and duration is limited by the ability of the patient to tolerate, or survive the therapy. 3) The side effects of systemic hypothermia are frequent and can be life threatening, especially in frail patients. Side effects include shivering, cardiac arrhythmia and arrest, pneumonia, infections, and coagulation disorders. 4) The target of hypothermia therapy is the brain; therefore inducing hypothermia systemically places the patient at undue risk. 5) During the "critical phase" (rewarming period) of hypothermia treatment, there is no effective way to manage a sudden and critical increase in intra-cranial pressure, since re-cooling the body to reverse the increase in intra-cranial pressure takes several hours. 6) Systemic hypothermia poses significant clinical and logistical patient management issues.

There are several examples in the art where catheters are constructed with a cooling means, which is placed into the carotid artery to cool the blood entering the head. This offers an advantage over systemic hypothermia, since it provides a means to cool the head to lower temperatures than the rest of the body, but it still results in systemic hypothermia. Also, since the scientific evidence suggests that hypothermia must be maintained for extended periods of time, there is a great risk that clots will form on the catheters and migrate into the brain leading to episodes of stroke.

Barbut et al. (U.S. Pat. No. 6,217,552) suggests that cerebral hypothermia may be accomplished by placing a catheter in a lateral ventricle of the brain, and a second catheter into the subarachnoid space, and then pumping cooled fluid from the first catheter in the lateral ventricle to the second catheter in the subarachnoid space where the fluid flows from the lateral ventricle, through the third ventricle, and into the subarachnoid space via the cerebral aqua duct. This approach may be effective in inducing cerebral hypothermia in a normal healthy brain; brains that are suffering ischemia or trauma are often swollen. Swelling of the brain compresses the ventricles and cerebral aqua duct which prevents or limits fluid flow between the lateral ventricle, and the subarachnoid space. One significant problem with inducing cerebral hypothermia by cooling the cerebrospinal fluid in the ventricles is that it results in systemic hypothermia due to the fact that the brain is highly vascular, and that up to $\frac{1}{5}$ of the body's heat is generated in the brain. Barut does not suggest a means of maintaining normal core temperature while inducing cerebral hypothermia by ventricle cooling. Another limitation of inducing cerebral hypothermia according to the method described by Barut is that the ventricle system is in the central region of the brain and that cooling the central region of the brain results in a temperature gradient within the brain where the surface of the brain remain significantly warmer than the central region of the brain. White et al. (Mayo Clinic Proceedings 53:450–458, 1978) induced cerebral hypothermia according to the method described by Barut et al. in a primate model. There was a 12 degree differential in temperature between the central region of the brain and the surface of the brain. Another limitation to the method of cerebral hypothermia as described by Barut is that in addition to placing a catheter into a lateral ventricle, a second catheter must be placed into the subarachnoid space. This results in additional surgical risk. A further limitation to the Barut method of inducing cerebral hypothermia is that cold fluid flowing through the third ventricle and cerebral aqua duct results cooling of the thalamus, hypothalamus and medulla, which suppresses the autonomic nervous system resulting in lower cardiac output and reduced cerebral blood flow. Ideally, the thalamus, hypothalamus, and medulla should be maintained at temperatures above 28 Degrees centigrade to prevent suppression of the autonomic nervous system.

Ventriculostomy is a common neurosurgical procedure that provides access to the lateral ventricles of the brain. The procedure is performed to drain excess CSF from the ventricles, to place physiological sensors into a ventricle, or to perform an endoscopic examination of a ventricle. Over 150,000 ventriculostomies are performed each year in the United States. Ventriculostomy is considered to be a very safe procedure with a very low serious complication rate.

Ventriculostomies are generally performed bed side in the ICU under local anesthesia. It is performed blindly without image guidance, and may be performed by neurosurgical residents. The procedure is performed by first making an incision in the scalp at a position determined by measurements from external landmarks of the head. After the incision, a small burr hole is drilled through the skull. The ventriculostomy catheter (usually a drainage catheter), in conjunction with a rigid introducer stylus is then advanced into the brain perpendicular to the skull. When the ventriculostomy catheter enters the ventricle, CSF being under slight pressure exits the proximal end of the catheter, which confirms proper catheter position. The catheter is then fastened to the scalp with suture, and the incision is then closed around the catheter shaft. Typically, drainage catheters are replaced every 5 days to reduce the risk of infection. It takes approximately 15 minutes place a ventricle drainage catheter.

Although ventriculostomies are generally performed in the ICU, there is no logistical obstacle to performing a ventriculostomy procedure in the Emergency Room.

Nowhere in the art is it suggested that cooling one or both lateral ventricles of the brain in combination with cooling the surface of the head may induce global cerebral hypothermia without significant temperature gradients within the brain and therefore prevent secondary brain injury. Nowhere in the art is it suggested that cerebral hypothermia can be accomplished by cooling a lateral ventricle using a single catheter. Nowhere in the art is a means taught for inducing selective cerebral hypothermia by ventricle cooling and surface cooling of the head and thermostatically controlled heating of the body core.

SUMMARY

Therefore, it is an object of this invention to provide a method and apparatus for preventing secondary brain injury by inducing selective cerebral hypothermia. In accordance with one aspect of this invention, brain cooling is accomplished by placing a cooling device(s) into one or both lateral ventricles of the brain and applying a surface-cooling device to the head, then cooling the ventricle(s) with the ventricle-cooling device(s) and cooling the surface of the head with the surface-cooling device. In accordance with another aspect of this invention, selective brain cooling is accomplished by placing a cooling device(s) into one or both lateral ventricles of the brain and applying a surface-cooling device to the head and applying a body-heating device to the body, then cooling the ventricle(s) with the ventricle-cooling device(s) and cooling the surface of the head with the surface-cooling device while simultaneously replacing the heat removed from the body by the ventricle-cooling device(s) and the surface-cooling device with the body-heating device. In accordance with another aspect of this invention, selective brain cooling is accomplished by placing a cooling catheter(s) into one or both lateral ventricles of the brain and fitting to the head a head-cooling cap and covering the body with an electric heating blanket and placing a body-core temperature sensor into the core of the body, then cooling the ventricle(s) with the ventricle-cooling catheter(s) and cooling the surface of the head with the head-cooling cap while simultaneously replacing the heat removed from the body by the ventricle-cooling catheter(s) and the head-cooling cap with the electric heating blanket where the heat applied to the body by the electric blanket is modulated to maintain normal body core temperature as sensed by the body-core temperature sensor. In accordance with another aspect of this invention, selective cerebral hypothermia is accomplished by placing a cooling catheter(s) into one or both lateral ventricles of the brain and fitting to the head a head-cooling cap and placing a heating catheter into the central venous system, then cooling the ventricle(s) with the ventricle-cooling catheter(s) and cooling the surface of the head with the head-cooling cap while simultaneously replacing the heat removed from the body by the ventricle-cooling catheter(s) and the head-cooling cap with the heating catheter where the heat applied to the body by the heating catheter is modulated to maintain normal body core temperature as sensed by a temperature sensor mounted on the heating catheter. In accordance with another aspect of this invention, apparatus for inducing cerebral hypothermia includes a ventricle-cooling device, a surface head-cooling device, and a control console that provides a cooling means for the ventricle-cooling device and the surface head-cooling device. In accordance with another aspect of this invention, apparatus for inducing selective cerebral hypothermia includes a ventricle-cooling device, a surface head-cooling device, a body core heating device, and a control console that provides a cooling means for the ventricle-cooling device and the surface head-cooling device and a heating means for the body-core heating device, and a means to control the cooling and the heating. In accordance with another aspect of this invention, apparatus for inducing selective cerebral hypothermia includes a ventricle-cooling catheter that is constructed to be placed into a ventricle by standard ventriculostomy means, to sense the temperature of the cerebrospinal fluid in a ventricle, to sense the pressure of cerebrospinal fluid in a ventricle, to drain excess cerebrospinal fluid from a ventricle and to cool cerebrospinal fluid in a ventricle. In accordance with another aspect of this invention, apparatus for inducing selective cerebral hypothermia includes a surface head-cooling cap that is constructed to be fitted to a patient's head by non-invasive means, to provide an opening in the cap to facilitate a ventriculostomy procedure, to provide a means for mounting cooling mechanisms for one or both lateral ventricle-cooling catheter(s) to the head, a means to sense the temperature of the surface of the head, and a means to cool a region of the surface of the head to a level that induces cerebral hypothermia. In accordance with another aspect of this invention, apparatus for inducing selective cerebral hypothermia includes a central venous heating catheter that is constructed to be placed into the superior vena cava, to sense the temperature of the blood in the superior vena cava, and to heat the blood in the superior vena cava as required to maintain normal body temperature as sensed by the temperature sensor. In accordance with another aspect of this invention, apparatus for inducing selective cerebral hypothermia includes a control console that is constructed to provide a means of cooling for one or more ventricle-cooling catheter(s), a means of cooling for a surface head-cooling cap, a means of heating for a central venous catheter, a means of heating for an electric heating blanket, and a means of controlling the cooling and the heating using physiological sensors placed on or within the body according to predetermined control algorithms and user settings.

OBJECTS AND ADVANTAGES

Accordingly, besides the objects and advantages of the method and apparatus to induce selective cerebral hypothermia to prevent secondary brain injury described in my patent above, several objects and advantages of the present invention are:

(a) to provide selective cerebral hypothermia to a brain at risk of secondary injury to the degree that offers maximum clinical benefit without clinically significant temperature gradients within the brain and without inducing hypothermia in the rest of the body;

(b) to provide selective cerebral hypothermia to a brain at risk of secondary injury to the degree that offers maximum clinical benefit without lowering the temperature of the thalamus, hypothalamus and medulla to a level where the autonomic nervous system is suppressed;

(c) to provide cerebral hypothermia to a brain at risk of secondary injury where the method for inducing hypothermia takes advantage of the fact that a lateral ventricle can be cooled by a catheter, and brain tissue surrounding the ventricle may be cooled by heat conduction into the walls of the ventricle, and that the surface of the head may be cooled with a head-cooling cap and that brain tissue near the surface of the head may be cooled by heat conduction through the skull into the head-cooling cap, and that combining the ventricle cooling with the surface cooling provides for cerebral hypothermia to the extent that prevents secondary injury without inducing clinically significant temperature gradients within the brain.

(d) to provide selective cerebral hypothermia to a brain at risk of secondary injury within a minimal time after patient presentation where therapeutic temperatures are achieved rapidly due to the fact that only the brain is cooled;

(e) to provide cerebral hypothermia by cooling a ventricle with a single catheter;

(f) to provide selective cerebral hypothermia to a brain at risk of secondary injury where the degree of hypothermia is adjusted according to the physiological response to hypothermia, where the physiological response to hypothermia is a change in intra-cranial pressure;

(g) to provide selective cerebral hypothermia to a brain at risk of secondary injury where the degree of hypothermia is adjusted according to the physiological response to hypothermia, where the physiological response to hypothermia is a change in patient symptoms.

(h) to provide selective cerebral hypothermia to a brain at risk of secondary injury where the degree of hypothermia is adjusted according to the physiological response to hypothermia, where the physiological response to hypothermia is a change in localized blood perfusion;

(i) to provide selective cerebral hypothermia to a brain at risk of secondary injury where the degree of hypothermia is adjusted according to the physiological response to hypothermia, where the physiological response to hypothermia is a change in the size of the volume of infarcted tissue;

(j) to provide selective cerebral hypothermia to a brain at risk of secondary injury where the degree of hypothermia is adjusted according to the physiological response to hypothermia, where the physiological response to hypothermia is a change in blood chemistry.

(k) to provide apparatus for inducing selective cerebral hypothermia to a brain tissue at risk of secondary injury according to the objectives stated above;

(l) to provide a brain cooling system that consists of at least one ventricle-cooling catheter constructed for use in a lateral ventricle, a head-cooling cap constructed to be mounted on the head, a heating catheter for use in the central vascular system, and a control console;

(m) to provide a brain cooling system that consists of at least one ventricle-cooling catheter constructed for use in a lateral ventricle, a head-cooling cap constructed to me mounted on the head, an electric heating blanket, a body-core temperature sensor, and a control console;

(n) to provide a ventricle-cooling catheter that is constructed to be placed into a lateral ventricle of the brain using well known surgical methods;

(o) to provide a ventricle catheter that has capability to drain CSF from a ventricle, measure the pressure within a ventricle, and cool the CSF within the ventricle;

(p) to provide a brain cooling system that is constructed to provide for long term cooling and indwelling;

(q) to provide a brain cooling system that is constructed to provide for a means to sense a response to cooling;

(r) to provide a brain cooling system that is constructed to provide for a means to control the degree of cooling applied to brain tissue;

(s) to provide a brain cooling system that is constructed to cool either a hemisphere of the brain, or the entire brain.

DRAWING FIGURES

Figure 8A:
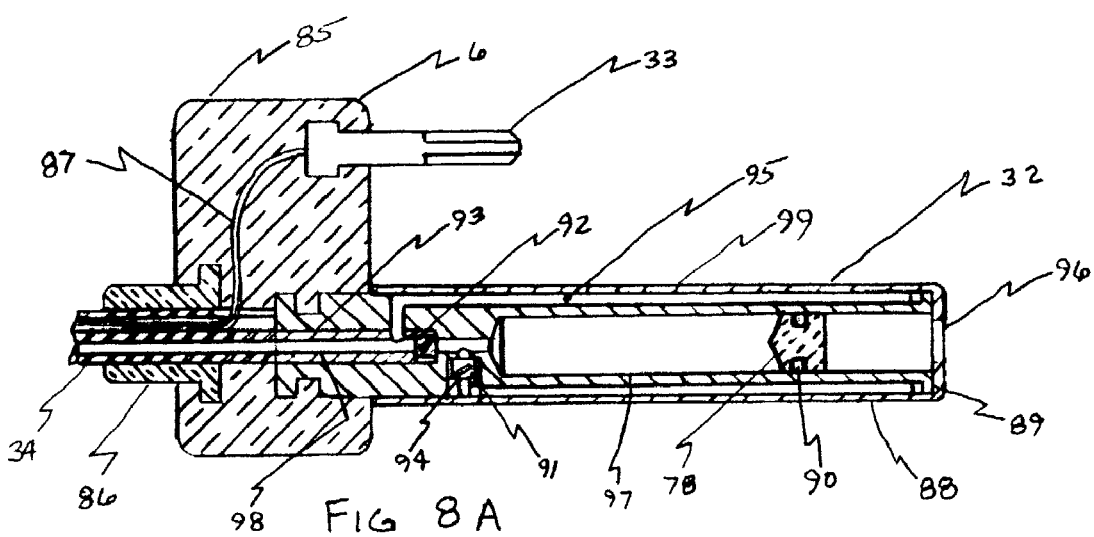
Figure 8B:
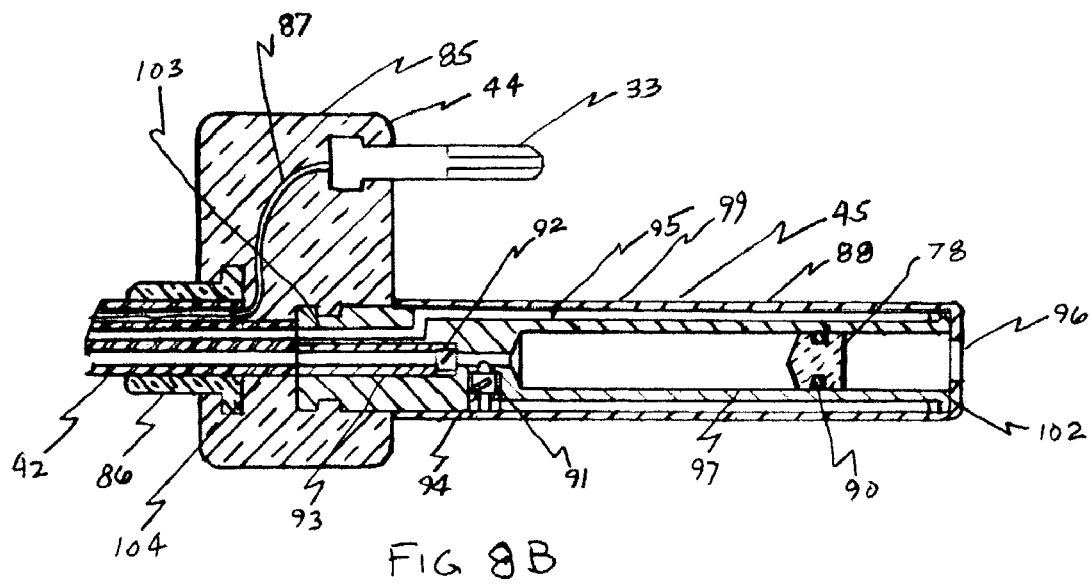
Figure 8C:
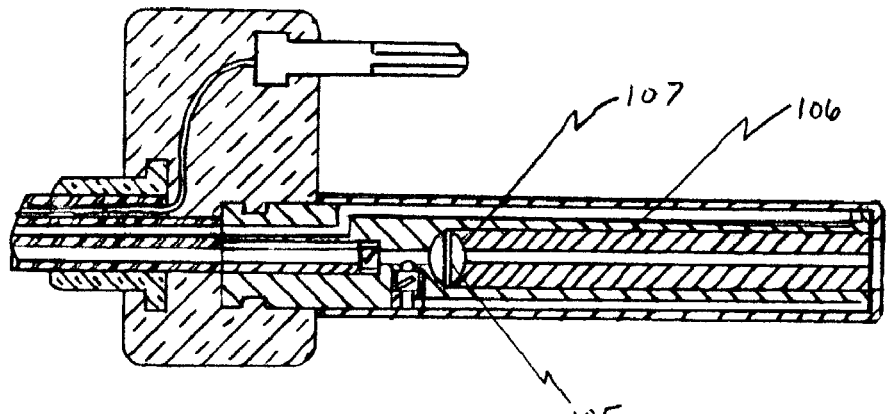

FIG. 8A depicts in sectional view the construction of the ventricle-cooling catheter cooling chamber designed for normal ventricles. FIG. 8B depicts in sectional view the construction of the ventricle-cooling catheter cooling chamber designed for compressed ventricles. FIG. 8C depicts in sectional view an alternate embodiment of the construction of the ventricle-cooling catheter cooling chamber designed for compressed ventricles.

FIG. 9 depicts the construction of the cooling chamber cooling tube.

Figure 10:
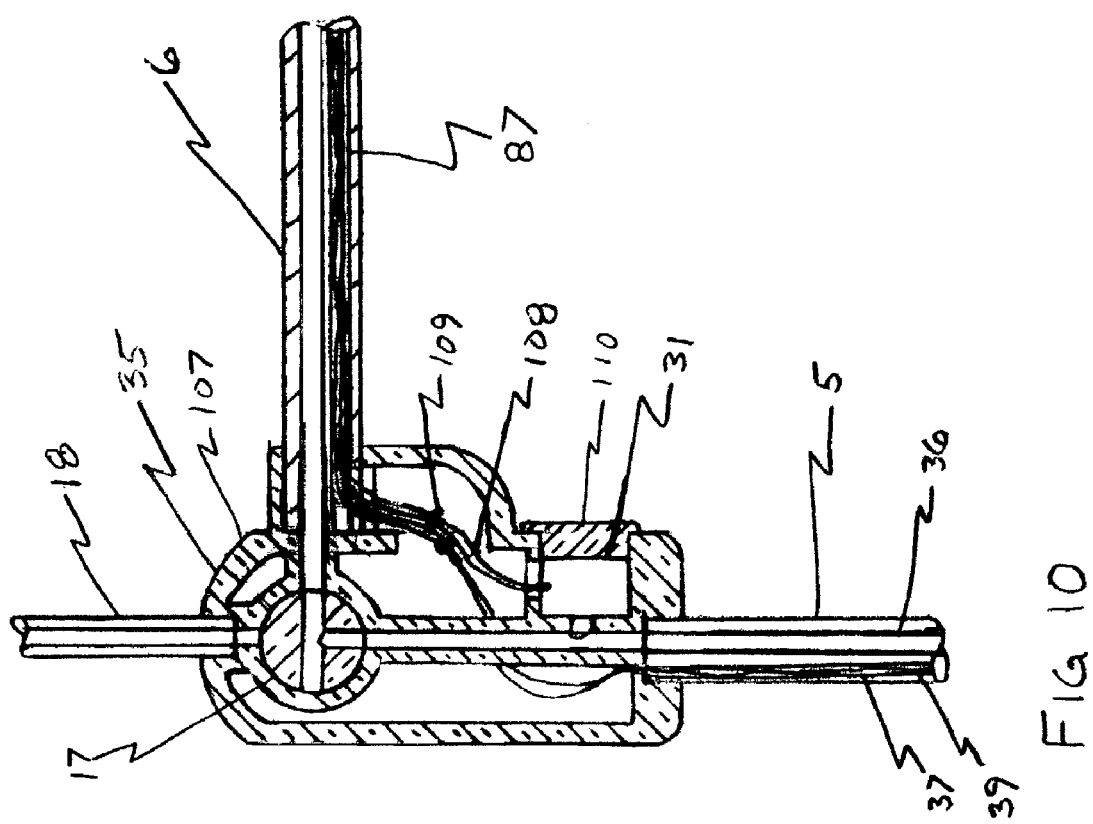

FIG. 10 depicts in sectional view the ventricle cooling-catheter stop-cock assembly.

Figure 11:
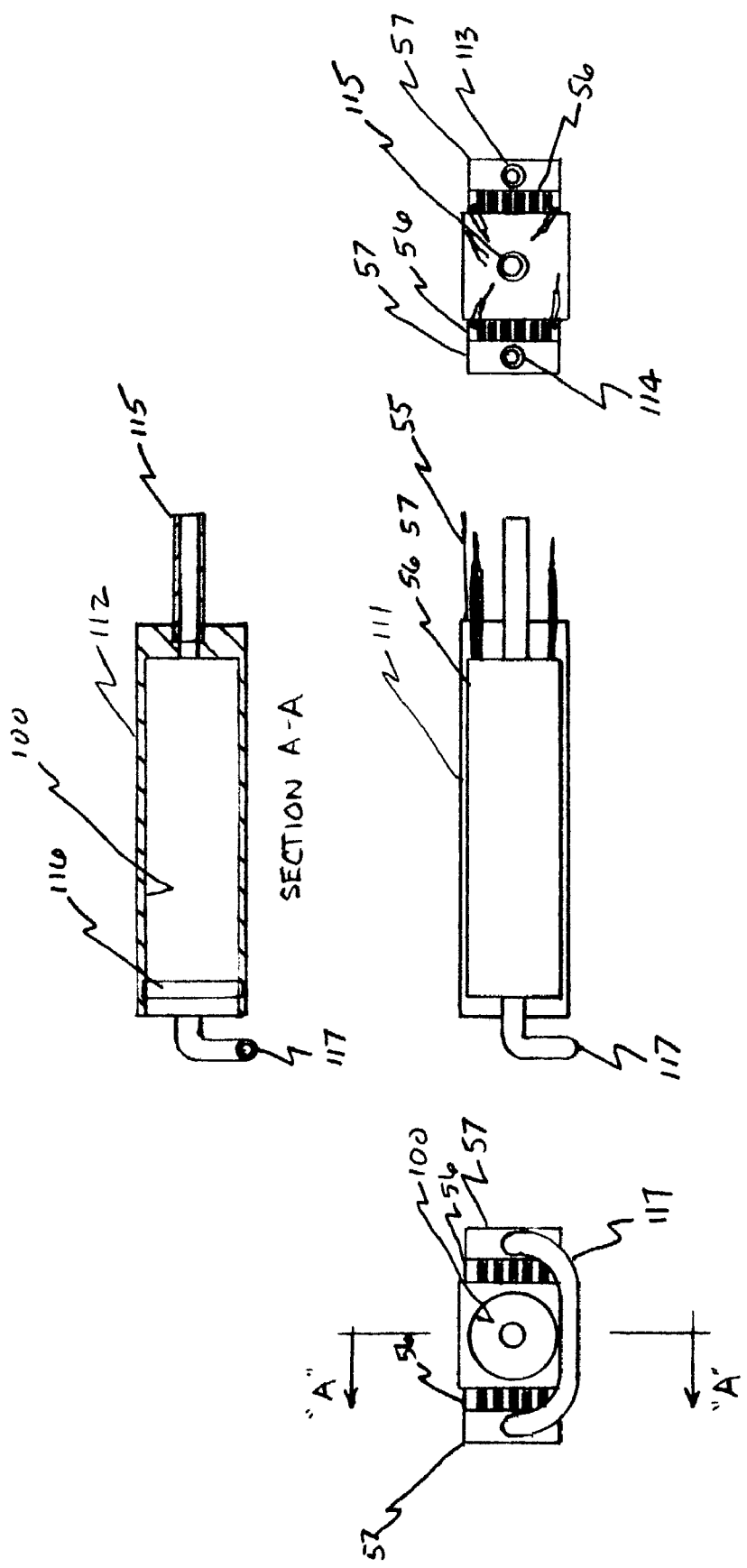

FIG. 11 depicts the construction of the cooling module cooling block assembly.

Figure 12:
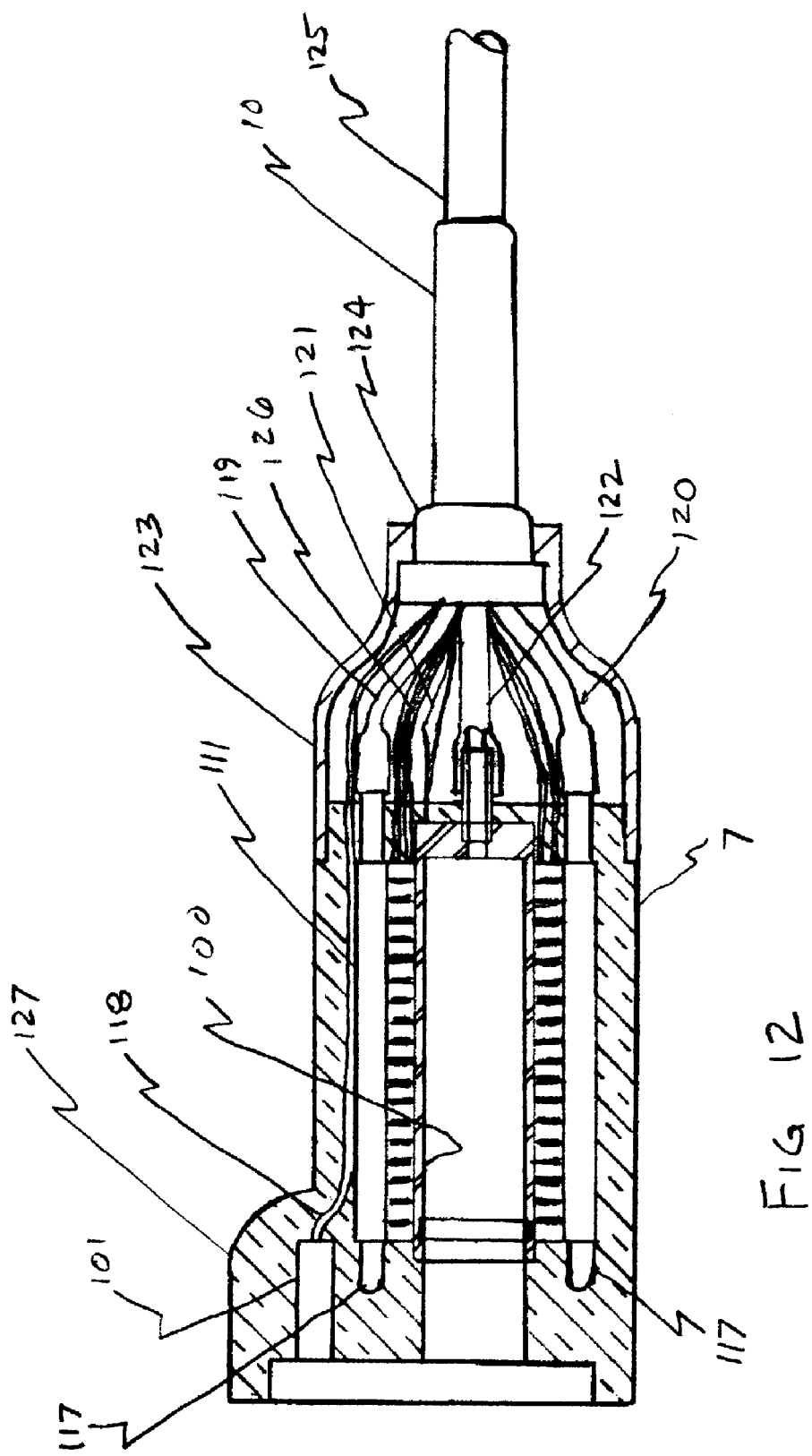

FIG. 12 depicts in sectional view the construction of the cooling module.

Figure 13:
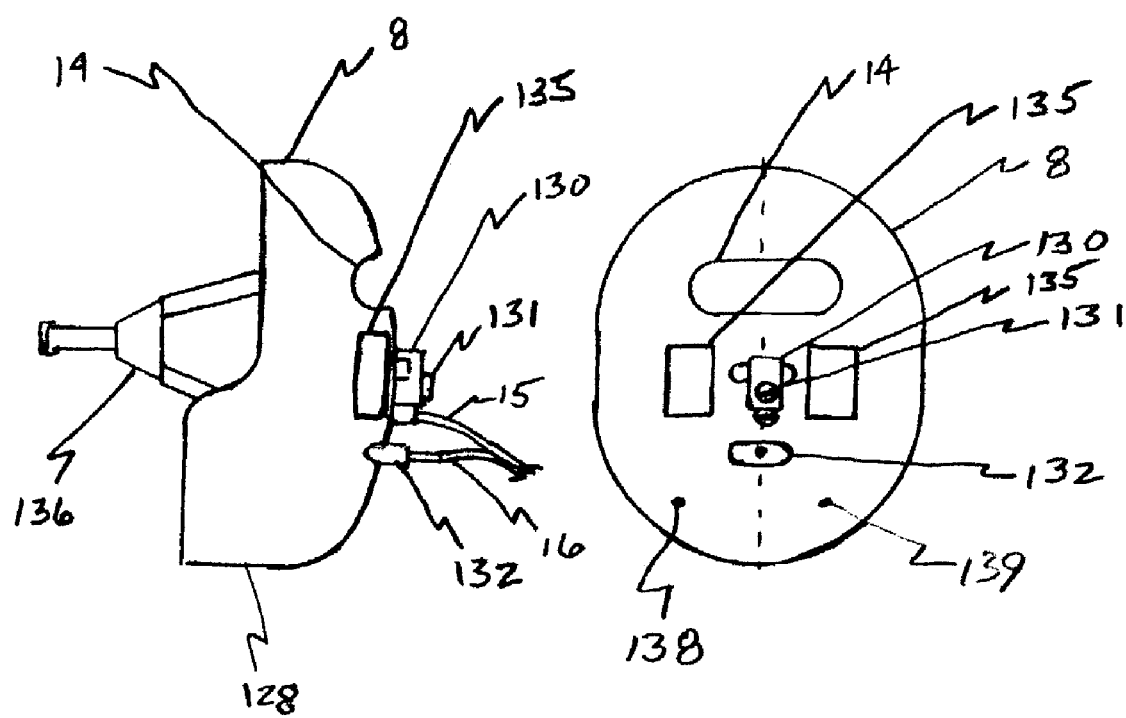

FIG. 13 depicts the head-cooling cap

Figure 14:
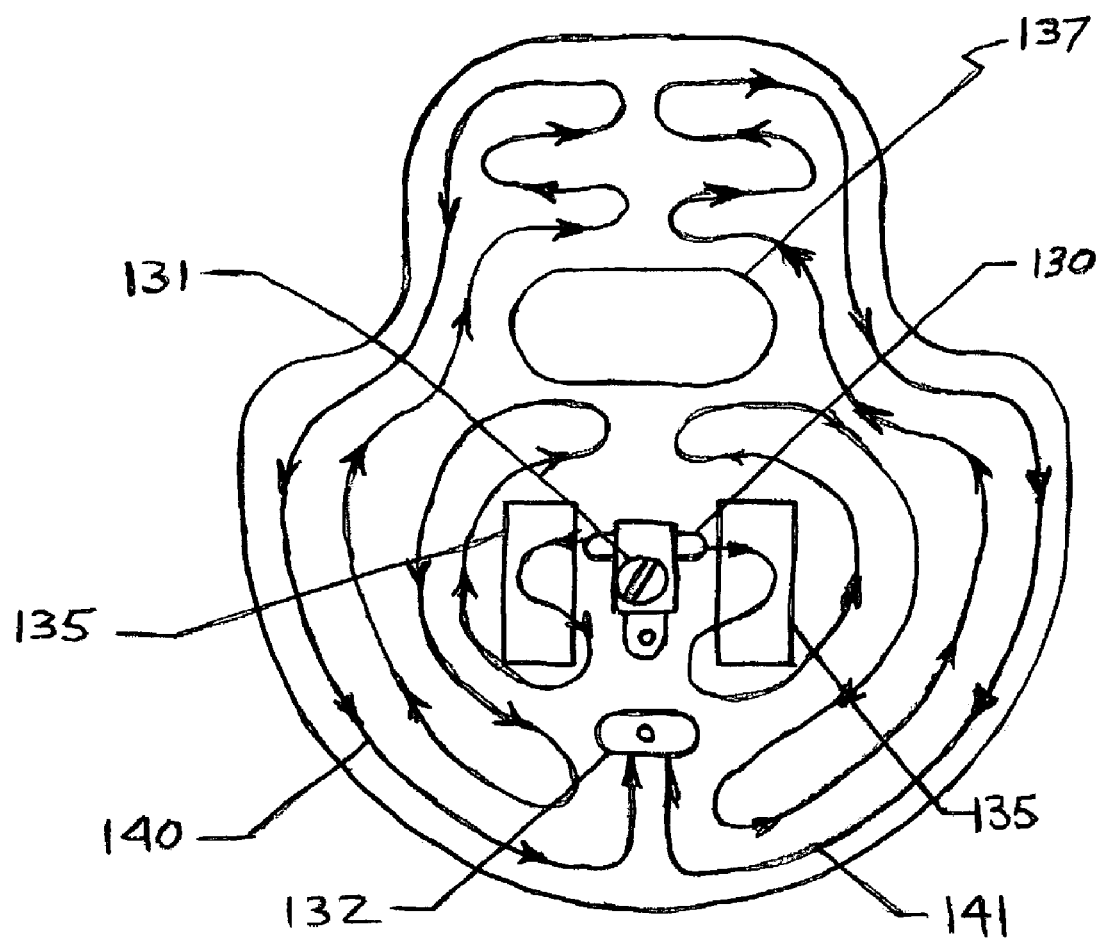

FIG. 14 depicts the fluid circulation within the head-cooling cap.

FIG. 15 depicts the head-cooling cap fluid control valve and the construction of the head-cooling cap.

DESCRIPTION—FIGS. 1–7—PREFERRED OPERATIONAL EMBODIMENTS

Figure 1:
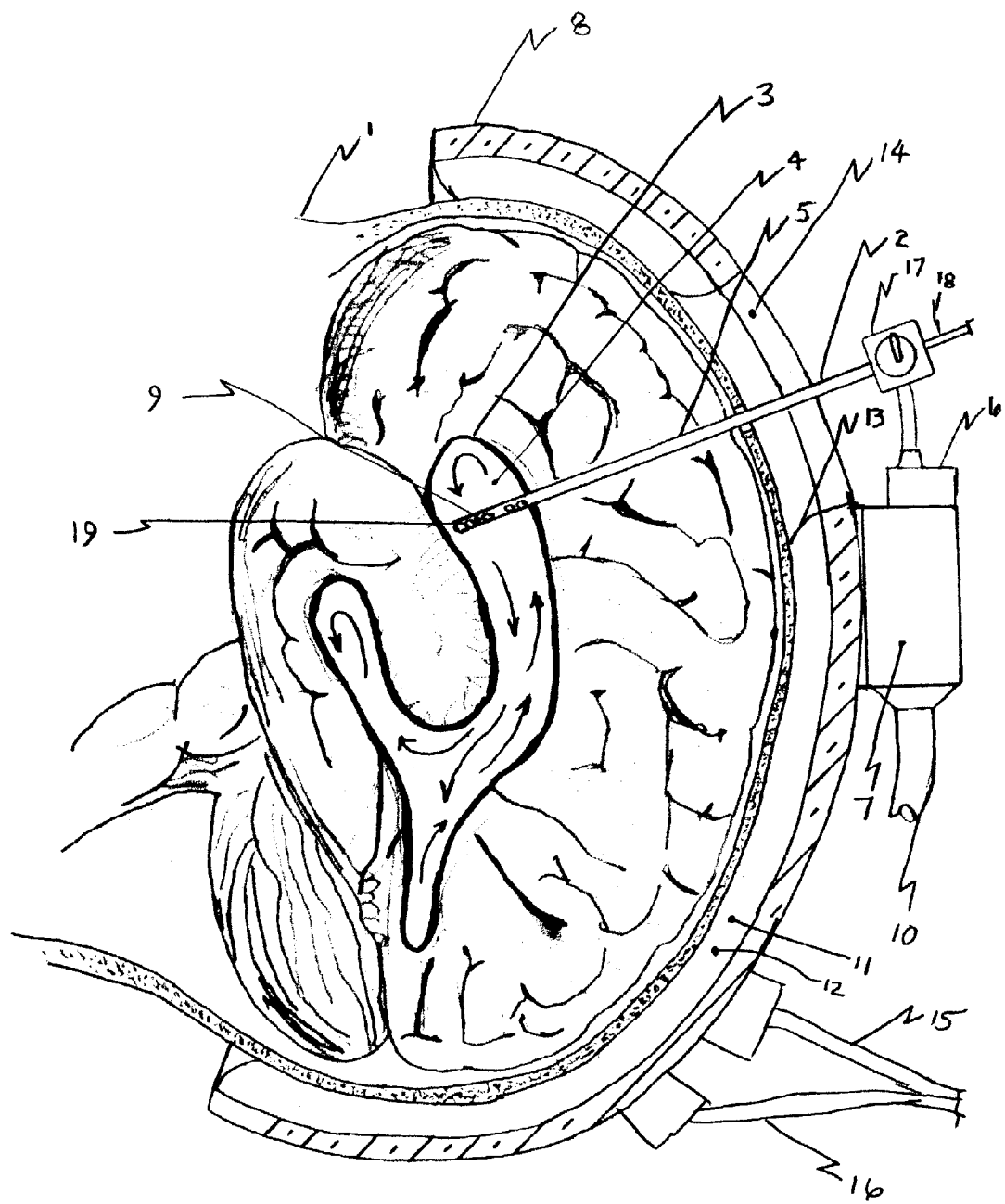
FIG. 1 depicts a sagittal section of the human head showing the ventricle-cooling catheter designed for a normal ventricle placed into a lateral ventricle of the brain, and the head-cooling cap mounted on the head.

FIG. 1 depicts a sagittal section of a human head 1 and the normal ventricle-cooling catheter 2 into a operational position in a lateral ventricle of the brain 3. Also shown is the head-cooling cap 8 mounted on the head 1. Cerebrospinal fluid (CSF) 4 is withdrawn from the lateral ventricle 3 through fluid ports 19 in ventricle-cooling catheter shaft 5 into ventricle cooling catheter cooling chamber assembly 6 which is then cooled by cooling module 7. Once the CSF is cooled, it is reinserted into lateral ventricle 3 through ventricle-cooling catheter shaft 5. This process is continued in a cyclical manner to obtain and maintain the target temperature of the CSF 4 in ventricle 3 as measured by temperature sensor 9 mounted on the distal end of ventricle-cooling catheter shaft 5. Cooling module 7 is connected to control console (not shown) by umbilical 10. Cooling module 7, cooling chamber assembly 6 and control console (not shown) work in operational relationship to withdraw CSF 4 from lateral ventricle 3, to cool a portion of CSF 4 ex vivo, and to reinsert cooled portion of CSF 4 back into ventricle 3. Ventricle-cooling catheter shaft 5 has a single lumen which is used to withdraw CSF 4 from ventricle 3 and reinsert CSF 4 into ventricle 3. Free convection (represented by arrows) provides for even temperature distribution within a normal ventricle 3. Stop cock 17 allows for CSF 4 to be either drained externally through drainage port 18, or cooled within cooling chamber assembly 6. This provides the ventricle cooling catheter 2 with the same functionality as a standard ventricle drainage catheter. The external surface of the head 1 is cooled by head-cooling cap 8 by circulation of cold fluid through fluid channels that are integral with the inner liner 13 of the head-cooling cap. The head-cooling cap 8 has an opening 14 that allows for placement and removal of one or two ventricle-cooling catheter(s) 2 while the head-cooling cap 8 is mounted to the head 1. Cold fluid 11 is cooled and circulated through the fluid channels 12 within the inner liner 13 by a pump and refrigeration mechanism located in the control console (not shown). Cold fluid 11 is supplied from the control console (not shown) by fluid supply tube 15, and is returned to the control console (not shown) by fluid return tube 16. The head-cooling cap is fixated to the head 1 with a chin strap (not shown).

Figure 2:
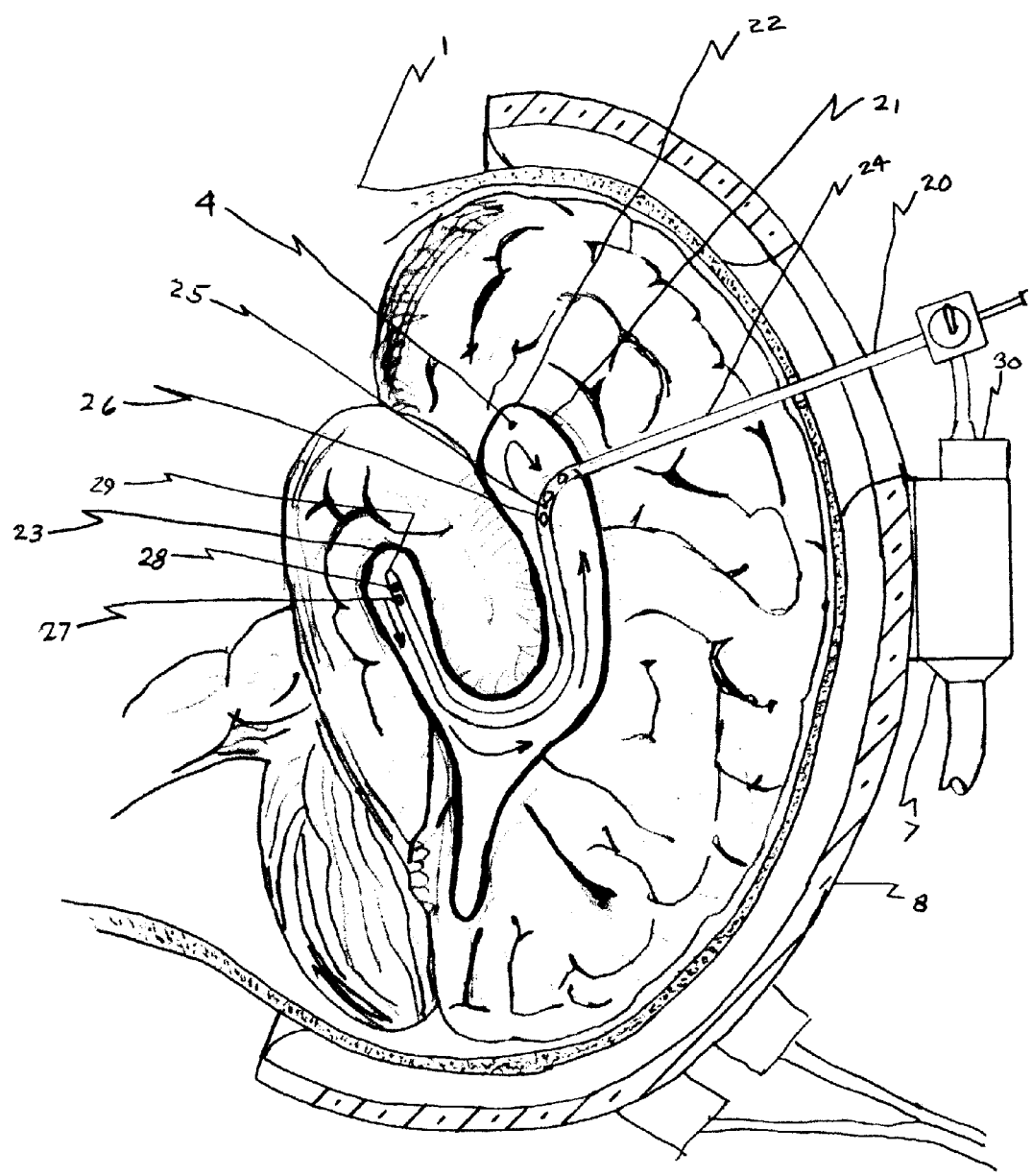
FIG. 2 depicts a sagittal section of the human head showing the ventricle-cooling catheter designed for a compressed ventricle placed into a lateral ventricle of the brain, and the head-cooling cap mounted on the head.

FIG. 2 depicts a sagittal section of a human head 1 with the compressed ventricle-cooling catheter 20 in operational position in a lateral ventricle of the brain 3. The compressed ventricle-cooling catheter is placed into a compressed lateral ventricle by standard fluoroscopically guide ventriculostomy technique such that the distal end 29 of the compressed ventricle-cooling catheter resides in the inferior horn 23 of compressed lateral ventricle 21. (Lateral ventricles become compressed when intracranial pressure is elevated due to edema or intracranial hemorrhage.) Proximal to the distal end 29 of compressed ventricle cooling catheter 20 are several CSF aspiration ports 26. Near the distal end 29 are several CSF infusion ports 27. CSF 4 is withdrawn from compressed lateral ventricle 21 through aspiration ports 26 into cooling chamber assembly 30 through compressed ventricle-cooling catheter shaft 24 and is then cooled by cooling module 7. Once the CSF is cooled, it is reinserted into compressed lateral ventricle 21 through compressed ventricle-cooling catheter shaft 24 and infusion ports 27 at the distal end 29 of catheter shaft 24. This process is continued in a cyclical manner to obtain and maintain the target temperature of the CSF 4 in compressed ventricle 3 as measured by temperature sensor 25 mounted on the compressed ventricle-cooling catheter shaft 24. Cooling module 7 is connected to control console (not shown) by umbilical 10. Cooling module 7, cooling chamber 30 and control console (not shown) work in operational relationship to withdraw CSF 4 from compressed lateral ventricle 21, to cool a portion of CSF 4 ex vivo, and to reinsert cooled portion of CSF 4 back into compressed ventricle 21. Flow of cooled CSF 4 (represented by arrows) from the inferior horn 23 to the anterior horn 22 provides for even temperature distribution within compressed lateral ventricle 21. The function of the head-cooling cap 8, cooling module 7, stopcock 17 and drainage port 18 are described in the FIG. 1 description above.

Figure 3:
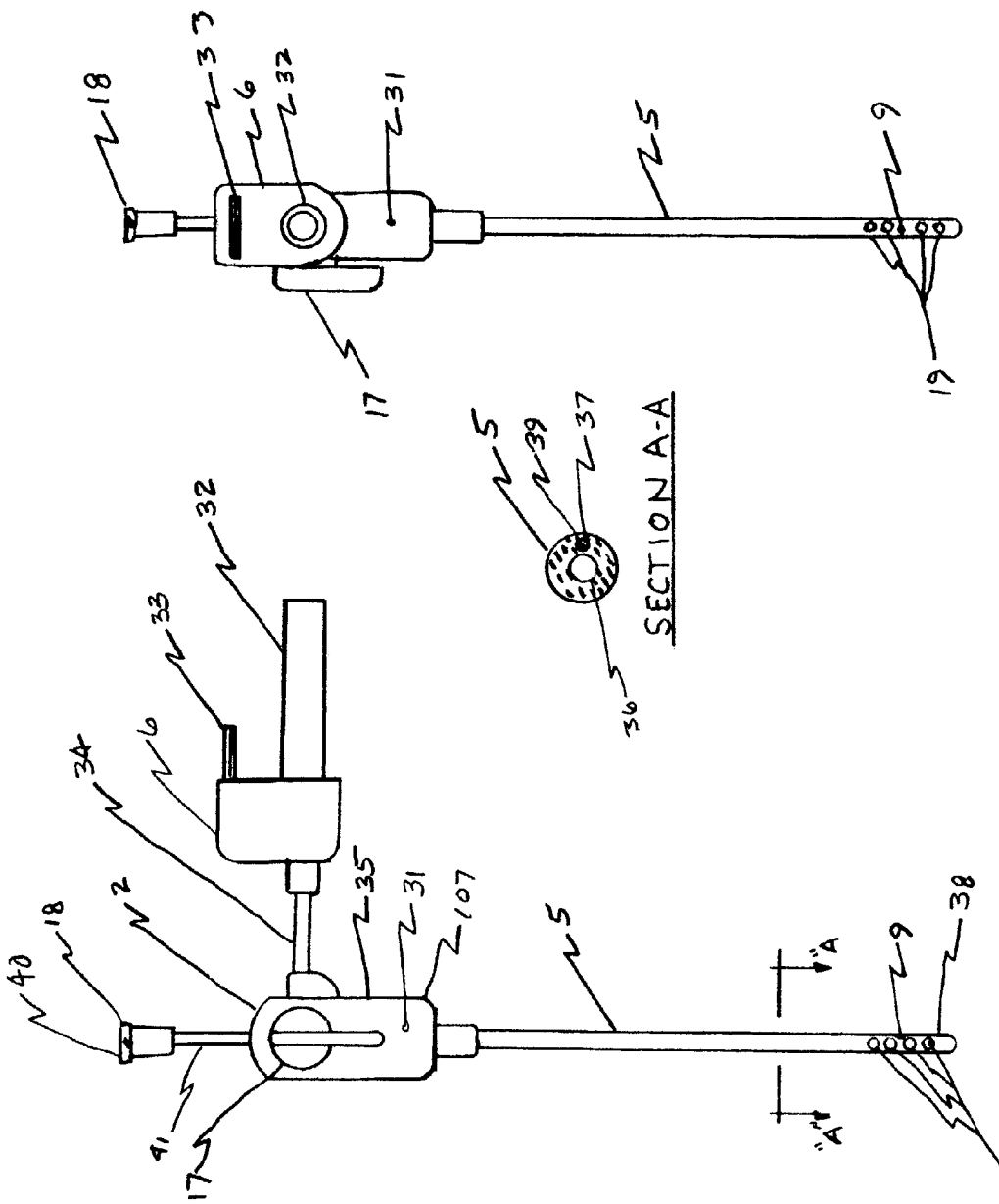
FIG. 3 depicts the ventricle-cooling catheter designed for normal ventricles.

FIG. 3 depicts the functional components of the normal ventricle-cooling catheter 2. The functional components of the ventricle-cooling catheter 2 are: catheter shaft 5, temperature sensor 9, fluid ports 19, pressure sensor 31, stopcock 17, CSF drainage port 18, stopcock/pressure sensor housing 35, connector tube 34, cooling chamber assembly 6 consisting of electrical connector 33 and heat exchanger/pump assembly 32. Catheter shaft 5 is made from silicone rubber and is 3 mm in diameter. Catheter shaft 5 has a central lumen 36 that is 1.5 mm in diameter and is used to transport CSF between the distal end 38 and the stopcock/pressure sensor housing 35. Catheter shaft 5 also has a temperature sensor lumen 37 that is 0.5 mm in diameter and contains the temperature sensor 9 and temperature sensor electrical leads 39. The distal end of catheter shaft 5 has several fluid ports 19 that provides communication of CSF 4 from the ventricle and central lumen 36. Stopcock housing contains 3-way stopcock 17 and pressure sensor 31 (not shown) and provides CSF 4 communication between central lumen 36 of catheter shaft 5, cooling chamber assembly 6, and CSF drainage port 18. Stopcock 17 provides switchable CSF 4 communication in the following manner: 1)3-way CSF 4 communication between central lumen 36 of catheter shaft 5, cooling chamber assembly 6, and CSF drainage port 18. 2) 2-way CSF 4 communication between central lumen 36 of catheter shaft 5 and cooling chamber assembly 6 3) 2-way CSF 4 communication between CSF drainage port 18 and central lumen 36 of catheter shaft 5. Pressure sensor 31 (not shown) senses CSF 4 pressure in central lumen 36 of catheter shaft 5. CSF drainage port 18 is a single lumen tube 41 with a female luer fitting 40. Connection tube 34 connects stopcock assembly 35 to cooling chamber assembly 6 and has a lumen for CSF 4 entry and exit into cooling chamber assembly 6 and a single lumen that contains electrical leads from temperature sensor 9 and pressure sensor 31. Cooling chamber assembly 6 contains electrical connector 33 and heat exchanger/pump assembly 32. Electrical connector 33 and heat exchanger/pump assembly 32 plug into corresponding receptacles in cooling module 7 (FIGS. 1 & 2). Electrical connector 33 connects temperature sensor 9 and pressure sensor 31 to control console (not shown) via cooling module umbilical 10 (FIGS. 1 & 2). Heat exchanger/pump assembly 32 contains a heat exchanger that transfers heat from CSF 4 into cooling module 7 by means of a cooling mechanism contained in cooling module 7, and a pump mechanism that is actuated by cooling module 7 to withdraw CSF 4 from a lateral ventricle through the heat exchanger and to reintroduce the cooled CSF 4 back into the ventricle. The heat exchanger and pump mechanism is designed to cool CSF 4 10 to 20 degrees centigrade at a flow rate of 20 ml/min to 80 ml/min.

Figure 4:
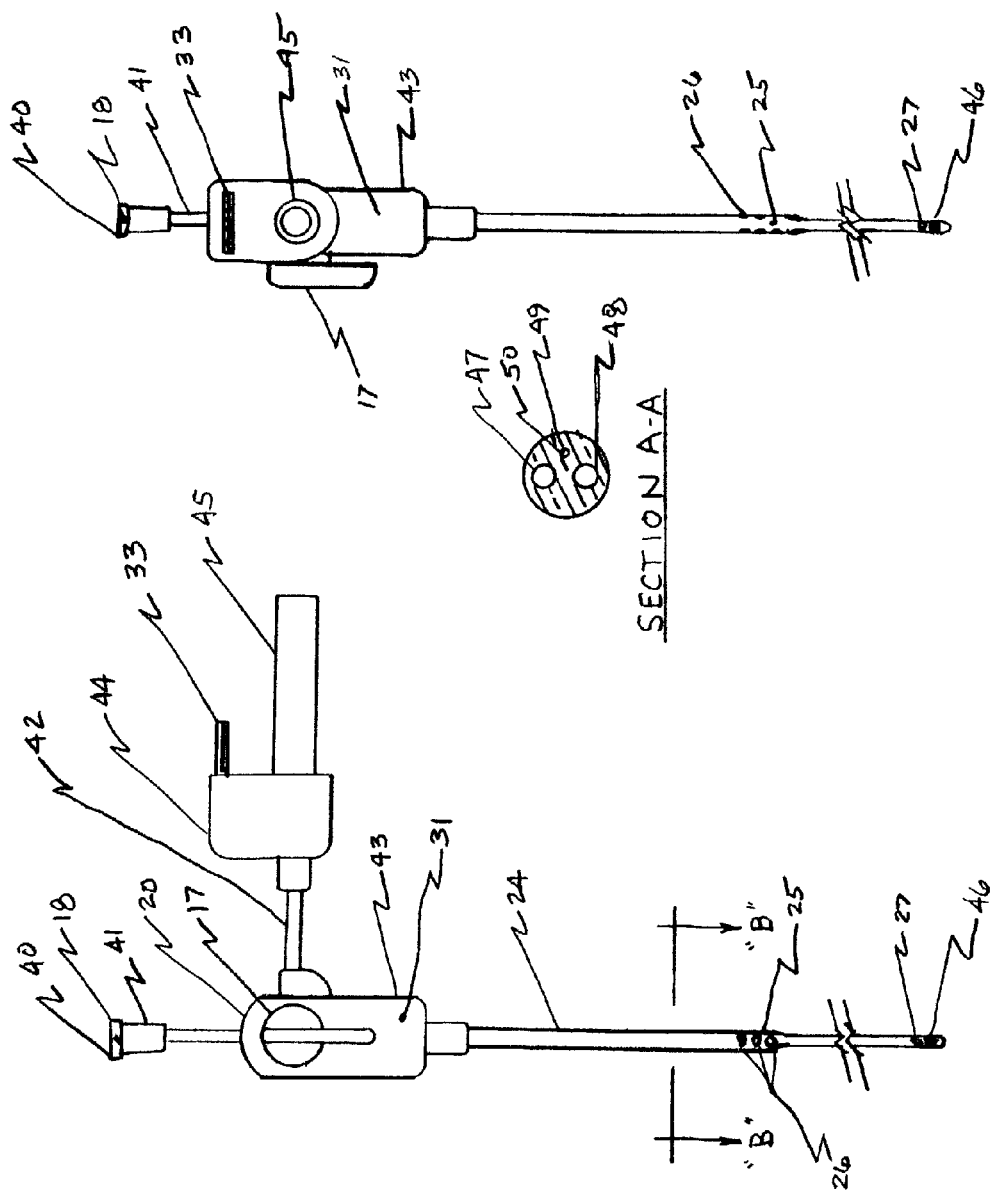
FIG. 4 depicts the ventricle-cooling catheter designed for compressed ventricles

FIG. 4 depicts the functional components of the compressed ventricle-cooling catheter 20. The functional components of the compressed ventricle-cooling catheter 20 are: catheter shaft 24, temperature sensor 25, CSF aspiration ports 26, pressure sensor 31, stopcock 17, CSF drainage port 18, stopcock/pressure sensor housing 43, connector tube 42, cooling chamber assembly 44 consisting of electrical connector 33 and heat exchanger/pump assembly 45. Catheter shaft 24 is made from silicone rubber and is 3 mm in diameter. Catheter shaft 24 has an aspiration lumen 47 that is 1.2 mm in diameter and is used to aspirate CSF from a lateral ventricle into the cooling chamber assembly 44 though stopcock housing 43 and connector tube 42. Catheter shaft 24 has an infusion lumen 48 that is 1.2 mm in diameter and is used to infuse cooled CSF into a lateral ventricle from the cooling chamber assembly 45 though stopcock housing 43 and connector tube 42. Catheter shaft 24 also has a temperature sensor lumen 49 that is 0.5 mm in diameter and contains the temperature sensor 25 and temperature sensor electrical leads 50. The distal end of catheter shaft 24 has several infusion ports 27 that provides communication from infusion lumen 48 and a lateral ventricle. Proximal to the distal end of catheter shaft 24 there are several aspiration ports 26 that provides communication from aspiration lumen 47 and a lateral ventricle. Stopcock housing 43 contains 3-way stopcock 17 and pressure sensor 31 (not shown) and provides CSF 4 communication between aspiration lumen 47 of catheter shaft 24, cooling chamber assembly 44, and CSF drainage port 18. Stopcock 17 provides switchable CSF 4 communication in the following manner: 1) 3-way CSF 4 communication between aspiration lumen 47 of catheter shaft 24, inlet of cooling chamber assembly 44, and CSF drainage port 18. 2) 2-way CSF 4 communication between aspiration lumen 47 of catheter shaft 24 and inlet of cooling chamber assembly 44 3) 2-way CSF 4 communication between CSF drainage port 18 and aspiration lumen 47 of catheter shaft 24. Stopcock assembly 43 contains a fluid passage between the outlet of cooling chamber assembly 44 and infusion lumen 48. Pressure sensor 31 (not shown) senses CSF 4 pressure in aspiration lumen 47 of catheter shaft 24. CSF drainage port 18 is a single lumen tube 41 with a female luer fitting 40. Connection tube 42 connects stopcock assembly 43 to cooling chamber assembly 44 and has an inlet lumen for CSF 4 entry into cooling chamber assembly 44, and outlet lumen for CSF 4 to exit cooling chamber assembly 44 and a single lumen that contains electrical leads from temperature sensor 25 and pressure sensor 31. Cooling chamber assembly 44 contains electrical connector 33 and heat exchanger/pump assembly 45. Electrical connector 33 and heat exchanger/pump assembly 45 plug into corresponding receptacles in cooling module 7 (FIGS. 1 & 2). Electrical connector 33 connects temperature sensor 25 and pressure sensor 31 to control console (not shown) via cooling module umbilical 10 (FIGS. 1 & 2). Heat exchanger/pump assembly 45 contains a heat exchanger that transfers heat from CSF 4 into cooling module 7 by means of a cooling mechanism contained in cooling module 7, and a pump mechanism that is actuated by cooling module 7 to withdraw CSF 4 from a lateral ventricle through aspiration lumen 47 into heat exchanger/pump assembly 45 and to reintroduce the cooled CSF 4 back into the ventricle through infusion lumen 48. The heat exchanger and pump mechanism is designed to cool CSF 4 10 to 20 degrees centigrade at a flow rate of 20 ml/min to 80 ml/min. Radiopaque marker 46 identifies the location of the distal end 38 of catheter shaft 24 during placement of compressed ventricle-cooling catheter 20 into compressed lateral ventricle 21 (FIG. 2).

Figure 5:
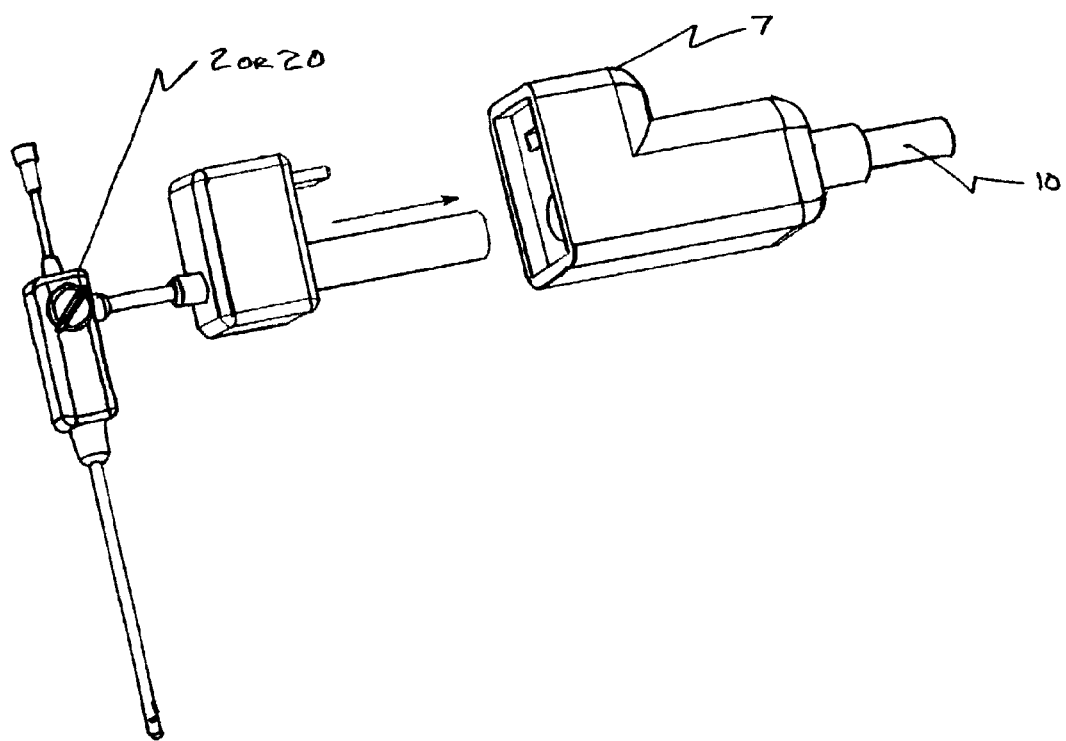
FIG. 5 depicts a ventricle-cooling catheter in operational relationship with a cooling module.

FIG. 5 depicts the operative relationship between the normal ventricle-cooling catheter 2 or the compressed ventricle cooling catheter 20 and the cooling module 7. Cooling module 7 is connected to the control console (not shown) by umbilical 10.

Figure 6:
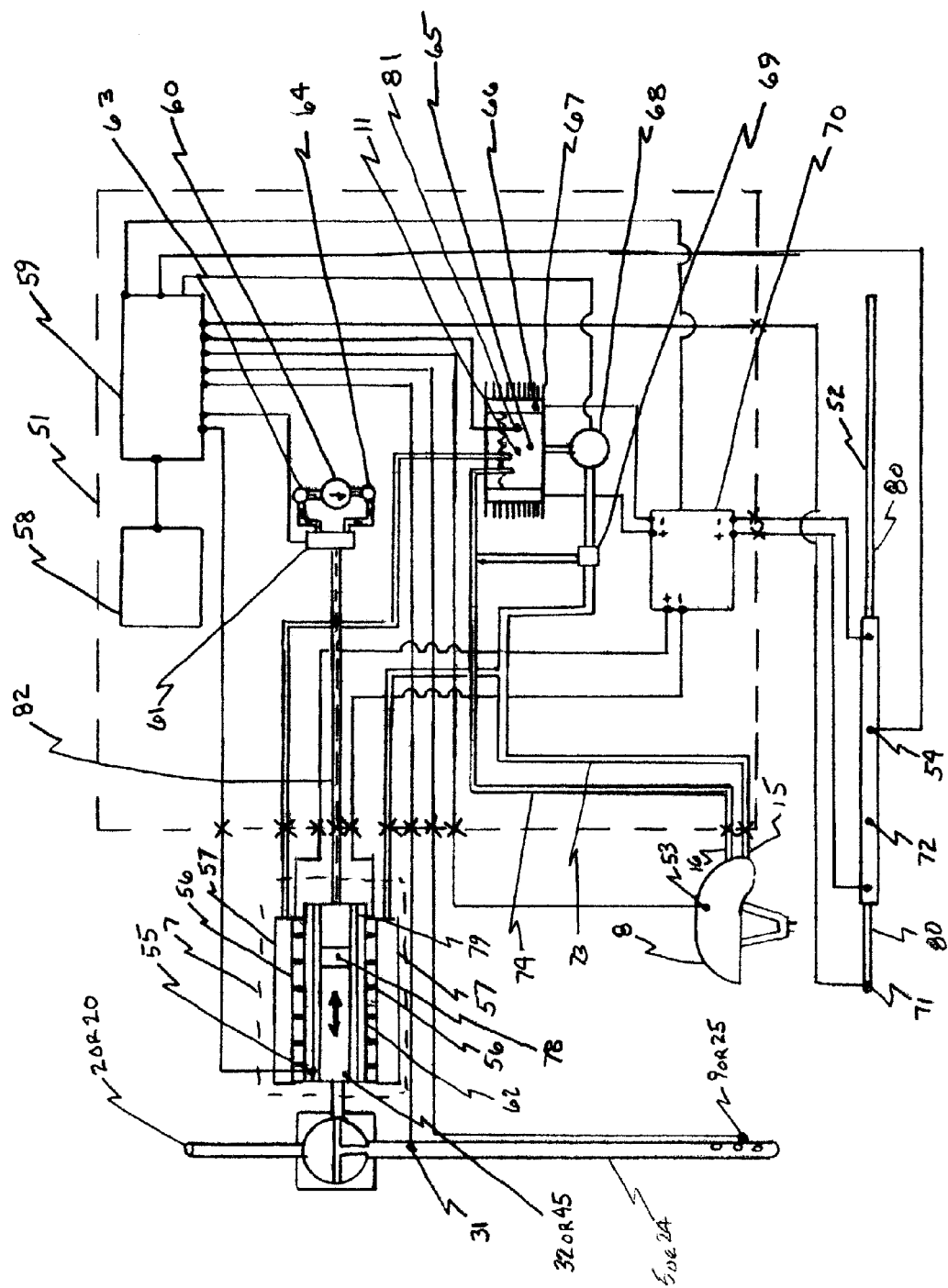
FIG. 6 depicts in schematic form the selective cerebral hypothermia system showing the operational relationships between the ventricle cooling catheter, head cooling cap, central venous heating catheter, and system control console.

FIG. 6 depicts the operation of one embodiment of the selective brain cooling system in schematic form. The selective brain cooling system consists of at least one ventricle-cooling catheter (2 or 20), a control console 51, and cooling module 7. In addition the system may include the following components: head-cooling cap 8, and body-core warming catheter 52. Cooling module 7, head-cooling cap 8, and body-core warming catheter 52 are removable and connectable to the control console 51 as represented by (X) in FIG. 6. The functional components of the control consol 51 are: control panel 58, motherboard 59, air pump 60, vacuum cylinder 63, pressure cylinder 64, shuttle valve 61, fluid reservoir 65, thermo-electric heat pump 66, radiator 67, fluid pump 68, pressure relief valve 69, and DC power supply 70. The functional components of the cooling module 7 are: temperature sensor 55, at least one thermo-electric heat pump 56, cooling block 62, and at least one heat exchanger 57. The functional components of the ventricle-cooling catheter (2 or 20) are: temperature sensor (9 or 25), pressure sensor 31, stop cock 17, heat exchanger/pump assembly (32 or 45) consisting of heat exchanger tube 79 and piston 78, and two check valves (not shown). The functional components of the cooling cap 8 are: fluid channels in walls (not shown), temperature sensor 53, fluid inlet tube 15, and fluid outlet tube 16. The functional components of body-core warming catheter 52 are: temperature sensor 71, electric heating element 72, temperature sensor 54, and catheter shaft 80. Control panel 58 contains user control switches, and informational displays for user operation of the system. The motherboard 59 contains a microprocessor and imbedded software and controls function of the system based on software algorithms, signals from temperature sensors (9 or 25), 55, 71, 54, 53, and 81, signals from pressure sensor 31, and from control panel 58 operator settings. Air pump 60 provides for pressure below atmosphere in vacuum cylinder 63, and pressure above atmosphere in pressure cylinder 64. Air pressure in vacuum cylinder 63, and air pressure in pressure cylinder 64 is maintained by pressure relief valves (not shown). Shuttle valve 61 is electrically actuated by motherboard 59 and applies either vacuum (air pressure below atmosphere) from vacuum cylinder 63, or pressure from pressure cylinder 64 to pneumatic line 82. Reservoir 65 contains water or some other cooling fluid 11. Fluid 11 within reservoir 65 is cooled by at least one thermo-electric heat pump 66 mounted on the walls of reservoir 65. Radiator 67 transfers heat removed from fluid in reservoir 65 by thermo-electric heat pump 66 into room air. A fan (not shown) may be used in conjunction with radiator 67 to increase heat transfer efficiency. Fluid pump 68 circulates fluid cooled in the reservoir 65 through the head-cooling cap 8, and heat exchanger(s) 57 in cooling module 7. Pressure relief valve 69 maintains fluid circulation pressure and returns excess fluid back to the reservoir. DC power supply 70 provides power for heating element 72 of body-warming catheter 52, thermo-electric heat pump(s) 56, and thermo-electric heat pump(s) 66. Temperature sensor (9 or 25) measures the temperature of CSF in a lateral ventricle and is used to control the amount of heat removed from CSF in heat exchanger/pump assembly (32 or 45) by cooling module 7, or the rate at which CSF is pumped through heat exchanger/pump assembly (32 or 45). Temperature sensor 71 of body-core warming catheter 52 measures the temperature of the blood in the right atrium of the heart or the superior vena cava and is used to control the amount of heat provided by heating element 72 to maintain the temperature of the blood entering the right atrium of the heart at normal body temperature (37 degrees centigrade). Temperature sensor 54 of body-core warming catheter 52 measures the temperature of the surface of heating element 72 and is used to ensure that the temperature of the surface of heating element 72 does not exceed a safe temperature of about 45 degrees centigrade. Temperature sensor 53 of head-cooling cap 8 measures the temperature of the surface of the scalp and is used to adjust the temperature of the cooling fluid 11 in reservoir 65 to maintain desired scalp surface temperature. Temperature sensor 81 of reservoir 65 measures the temperature of the cooling fluid 11 in reservoir 65 and is used to control the amount of heat removed from the fluid 11 in reservoir 65 by thermo-electric heat pump(s) 66 to maintain desired fluid 11 temperature. Pressure sensor 31 measures the pressure of CSF in catheter shaft (5 or 24) to detect out of parameter operation of the system and to provide for intracranial pressure (ICP) measurement between cycles. ICP pressure may be displayed on control panel 58. CSF 4 is pumped into and out of a ventricle by pneumatic actuation of pump piston 78 contained in heat exchanger/pump assembly (32 or 45) of ventricle-cooling catheter (2 or 20). (See FIG. 8 for operational and construction details of heat exchanger/pump assembly (32 or 45).) See FIGS. 11 & 12 for functional and construction details of cooling module 7. See FIGS. 13, 14 & 15 for functional and construction details of head-cooling cap 8. Body-core warming catheter 52 has a central lumen (not shown), and a luer fitting (not shown) on the proximal end to provide placement into the body by standard guidewire techniques.

Figure 7:
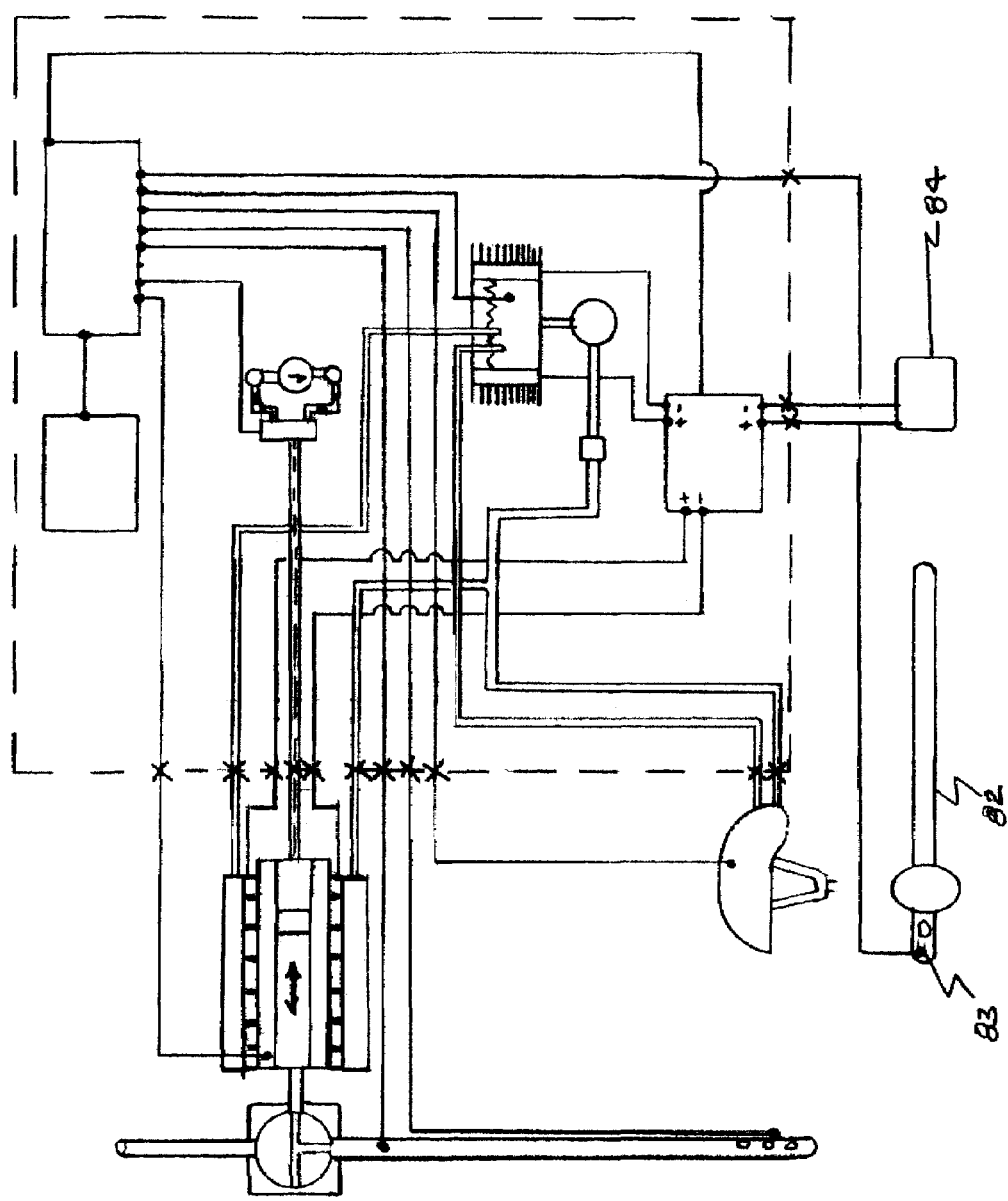
FIG. 7 depicts in schematic form the selective cerebral hypothermia system showing the operational relationships between the ventricle cooling catheter, head cooling cap, electric warming blanket, and system control console.

FIG. 7 depicts the operation of a second embodiment of the selective brain cooling system in schematic form. All component functionality remains as depicted in FIG. 6 with the exception that body core warming is accomplished by heating blanket 84 instead of body-core warming catheter 52 (FIG. 6). Body core temperature is measured by temperature sensor 83 that is mounted of Foley catheter 82. Foley catheter 82 is placed into the bladder of the patient and bladder temperature is used as a surrogate for body core temperature. Heat is applied to the electric blanket as required to maintain normal body temperature as sensed by temperature sensor 83.

Description FIGS. 8–15—Construction Details of Preferred Embodiments

FIG. 8A depicts in sectional view the construction of the cooling chamber assembly 6 for the normal ventricle-cooling catheter 2. Cooling chamber assembly 6 consists of heat exchanger/pump assembly 32, electrical connector 33, cooling chamber housing 85, strain relief 86, connector tube, 34, and electrical conduit 87. Heat exchanger/pump assembly 32 consists of outer cooling tube 88, inner cooling tube 89, piston 78, o-ring 90, check valve 91, check valve 92, check valve retainer 93, and check valve retainer 94. Piston 78 is actuated pneumatically by pneumatic apparatus 60, 61, 63, 64 in control console 51 (FIGS. 6 & 7). Pneumatic connection to control console 51 is by umbilical 10 and cooling module 7 (FIGS. 1, 2 & 5). When vacuum is applied through pneumatic port 96, piston 78 moves to the right. When pressure is applied through pneumatic port 96, piston 78 moves to the left. When piston 78 moves to the right, CSF is withdrawn from a lateral ventricle. When piston moves to the left CSF is reintroduced into a lateral ventricle. When piston 78 moves to the right, low pressure in the left side of cylinder 97 closes check valve 92 and opens check valve 91 causing CSF to enter cylinder 97 through circuitous fluid channel 95 formed in outside wall of inner cooling tube 89. When piston 78 moves to the left, high pressure in the left side of cylinder 97 opens check valve 92 and closes check valve 91 causing CSF to exit cylinder 97 through common fluid channel 98 and enter the lateral ventricle. Circuitous fluid channel 95 is formed by a milled channel in the outside wall of inner cooling tube 89, and by outer cooling tube 88. Outer cooling tube 88 and inner cooling tube 89 are preferably machined from a medical grade metal with high thermal conductivity such as silver. Inner cooling tube 89 and outer cooling tube 88 are soldered or welded together after piston 78 containing o-ring 90 have been inserted as shown in cylinder 97. Piston 78 travel is limited by the depth of cylinder 97, and outer cooling tube 88 as shown. A thin film of conductive thermal grease 99 is applied to the outside of outer cooling tube 88 at the factory to provide good thermal contact with cooling surface 100 (FIGS. 11 & 12) in cooling module 7 while maintaining a clearance fit between outer cooling tube 88 and cooling surface 100. The circuitous fluid path 95 is sized such that CSF flows through fluid path 95 in a turbulent manner so as to maximize heat transfer. Electrical connector 33 mates with electrical receptacle 101 (FIG. 12) and connects temperature sensor 9 (FIGS. 1, 3 & 6) and pressure sensor 31 (FIGS. 1, 3, & 6) to control console 51 (FIG. 6) using electrical conduit 87. Cooling chamber-housing 85 is formed by insert molding process using a thermoplastic material such as polycarbonate. Strain relief 86 prevents kinks in connector tube 34, and is made from an elastomer such as silicone rubber.

FIG. 8B depicts in sectional view the construction of the cooling chamber assembly 44 for the compressed ventricle-cooling catheter 20. Cooling chamber assembly 44 consists of heat exchanger/pump assembly 45, electrical connector 33, cooling chamber housing 85, strain relief 86, connector tube 44, and electrical conduit 87. Heat exchanger/pump assembly 45 consists of outer cooling tube 88, inner cooling tube 102, piston 78, o-ring 90, check valve 91, check valve 92, check valve retainer 93, and check valve retainer 94. Piston 78 is actuated pneumatically by pneumatic apparatus 60, 61, 63, 64 in control console 51 (FIGS. 6 & 7). Pneumatic connection to control console 51 is by umbilical 10 and cooling module 7 (FIGS. 2 & 5). When vacuum is applied through pneumatic port 96, piston 78 moves to the right. When pressure is applied through pneumatic port 96, piston 78 moves to the left. When piston 78 moves to the right, CSF is withdrawn from a lateral ventricle. When piston moves to the left CSF is reintroduced into a lateral ventricle. When piston 78 moves to the right, low pressure in the left side of cylinder 97 closes check valve 92 and opens check valve 91 causing CSF to enter cylinder 97 through inlet fluid channel 103 and circuitous fluid channel 95 formed in outside wall of inner cooling tube 102. When piston 78 moves to the left, high pressure in the left side of cylinder 97 opens check valve 92 and closes check valve 91 causing CSF to exit cylinder 97 through outlet fluid channel 104 and enter the lateral ventricle. Inlet fluid channel 103 is in fluid communication with aspiration ports 26 in compressed ventricle-cooling catheter 20 (FIG. 4). Outlet fluid channel 104 is in fluid communication with infusion port 27 in compressed ventricle-cooling catheter 20. Circuitous fluid channel 95 is formed by a milled channel in the outside wall of inner cooling tube 102, and by outer cooling tube 88. Inner cooling tube 102 and outer cooling tube 88 are preferably machined from a medical grade metal with high thermal conductivity such as silver. Inner cooling tube 102 and outer cooling tube 88 are soldered or welded together after piston 78 containing o-ring 90 have been inserted as shown in cylinder 97. Piston 78 travel is limited by the depth of cylinder 97, and outer cooling tube 88 as shown. A thin film of conductive thermal grease 99 is applied to the outside of outer cooling tube 88 at the factory to provide good thermal contact with cooling surface 100 (FIGS. 11 & 12) in cooling module 7 while maintaining a clearance fit between outer cooling tube and cooling surface 100. The circuitous fluid path 95 is sized such that CSF flows through fluid path 95 in a turbulent manner so as to maximize heat transfer. Electrical connector 33 mates with electrical receptacle 101 (FIG. 12) and connects temperature sensor 25 (FIGS. 2 & 4) and pressure sensor 31 (FIGS. 2 & 4) to control console 51 (FIG. 6) using electrical conduit 87. Cooling chamber-housing 85 is formed by insert molding process using a thermoplastic material such as polycarbonate. Strain relief 86 prevents kinks in connector tube 42, and is made from an elastomer such as silicone rubber.

FIG. 8C depicts an alternate embodiment for compressed ventricle-cooling catheter 20 cooling chamber assembly 44. In this embodiment elastomer diaphragm replaces 105 replaces piston 78 (FIG. 8B). Diaphragm 105 is retained with diaphragm retainer 106. Diaphragm 107 conforms to the right wall of pump camber 107 when vacuum is applied, and diaphragm 107 conforms to the left wall of pump camber 107 when pressure is applied which provides the pump mechanism.

FIG. 9 depicts the circuitous fluid channel 95 milled into surface if inner cooling tube 89 and 102 (FIGS. 8A & 8B).

FIG. 10 depicts in sectional view the construction of the stop cock assembly 107 for the normal ventricle-cooling catheter 2 (FIG. 3). Stop cock assembly 107 consists of cooling chamber assembly 6, catheter shaft 5, temperature sensor 9, temperature sensor electrical leads 39, pressure sensor 31, pressure sensor electrical leads 108, drainage port 18 consisting of single lumen tube 41 and luer fitting 40 (FIG. 3), stop cock 17, pressure sensor retainer 110, and stop cock housing 35. Stop cock housing 35 is injection molded of a thermoplastic material such as polycarbonate in two pieces and ultrasonically welded together to form sectional view as shown. Pressure sensor 31 is a common medical grade wheatstone bridge pressure transducer. Stop cock 17 rotates within stop cock housing provides 3 way fluid path selection as previously described. Temperature sensor leads 39 and pressure sensor leads 108 are connected to electrical conduit 87 of cooling chamber assembly 6 (FIG. 8A) using solder and insulators 109. Connector tube 34 of cooling chamber assembly 6, catheter shaft 5 and CSF drainage port 18 are glued into position shown using RTV adhesive. Pressure sensor retainer 110 is also glued into position using an adhesive.

FIG. 11 depicts the construction of cooling block assembly 111 of cooling module 7 (FIGS. 1, 2, & 5). Cooling block assembly consists of: cooling block 112, at least one thermo-electric heat pump 56, at least one water-cooled heat sink 57, one inlet tube 113, one outlet tube 114, one pneumatic tube 115, one pneumatic seal 116 and temperature sensor 55. Manifold tube 117 is used when two thermo-electric heat pumps 56, and two water-cooled heat sinks are used as depicted. Cooling block 112 is machined from copper and cooling surface 100 is hard-gold plated for durability. Thermo-electric heat pumps are common peltier effect devices manufactured by Melcor Corp. of Trenton, N.J. Water-cooled heat sinks 57 are copper blocks with water channels running through the center of the blocks. The cold face of thermo-electric heat pumps 56 are soldered to cooling block 112 as shown. Water-cooled heat sinks 57 are soldered are soldered to the hot face of thermo-electric heat pumps 56 as shown. Inlet tube 113 is soldered to one water-cooled heat sink as shown. Outlet tube 114 is soldered to the second water-cooled heat sink 57 as shown. Manifold tube 117 is soldered to both water-cooled heat sinks as shown. Pneumatic tube 115 is soldered to cooling block 112 as shown. Tubes 113, 114, and 117 may be copper or stainless steel. Pneumatic seal 116 may be a rubber o-ring. Heat is transferred from the cooling surface 100 of cooling block 112 into the water-cooled heat sinks 57 by thermo-electric heat pumps 56. Heat is removed from the cooling module 7 by cold water 11 circulated through the water-cooled heat sinks 57 by control console 51 via umbilical 10.

FIG. 12 depicts in sectional view cooling module 7 and umbilical 10 (FIGS. 1, 2, & 5). Cooling module 7 consists of: cooling block assembly 111, umbilical assembly 10, electrical receptacle 110, and cooling module housing 127. Umbilical assembly 10 consists of: umbilical housing 123, electrical conduit 118, temperature sensor leads 121, thermo-electric heat pump leads 126, inlet tube, 119, outlet tube 120, pneumatic tube 122, strain relief 124, umbilical sheath 125 and control panel connector (not shown). Cooling module housing is insert molded using a thermoplastic material such as polycarbonate over cooling block assembly 111 and electrical receptacle 101 as shown after electrical conduit 118 is connected to electrical receptacle 101. Inlet tube 119 is connected to inlet tube 113 of cooling block assembly 111. Outlet tube 120 is connected to outlet tube 114 of cooling block assembly 111. Pneumatic tube 122 is connected to pneumatic tube 115 of cooling module assembly 111. Temperature sensor leads 121 is connected to temperature sensor 55 of cooling block assembly using solder and insulators(not shown) thermo-electric heat pump leads 126 are connected to thermo-electric heat pumps 56 of cooling block assembly 111 with solder and insulators (not shown). Strain relief housing 123 is injection molded from a thermoplastic such as polycarbonate and is ultrasonically welded to cooling module housing 127 as shown. Strain relief housing 123 mechanically retains strain relief 124 and umbilical sheath 125 as shown. Control panel connector (not shown) is assembled to the opposite end of cooling module umbilical 10.

FIG. 13 depicts the functional components of cooling cap 8 (FIGS. 1, 2, 6 & 7). The functional components of the head-cooling cap 8 consist of: outer liner 128, inner liner (not shown—See FIG. 15), inlet manifold 130, flow control valve 131, outlet manifold 132, inlet tube 15, outlet tube 16, cooling module retaining bracket 135, chin strap 136, and ventricle cooling catheter opening 14. Fluid channels are formed between outer liner 128 and inner liner (not shown—See FIG. 15). Outer liner 128 and inner liner (not shown) are constructed from either silicone rubber, or a thermoplastic such as polyethylene. Head cooling cap 8 has two fluid channels 140 & 141 (FIG. 14); fluid channel 140 on the left side 138, and fluid channel 141 on the right side 139. Cold fluid 11 is circulated through one or both fluid paths by the control console to cool the scalp of the head. Inlet manifold 130 and flow control valve 131 direct cooling fluid 11 through either left fluid channel 140, or right fluid channel 141 (FIG. 14) or both fluid channels 140 & 141 to cool either the left side of the head, the right side of the head or both sides of the head respectively. This feature, in combination with ventricle cooling provides for either hemispheric cerebral hypothermia, or global cerebral hypothermia. Inlet tube 15 supplies cooling fluid 11 to the flow control valve 131 and inlet manifold 130 from control console 51 (FIGS. 6 & 7). Outlet manifold 132 connects to the outlet end of left fluid channel 140, and outlet end of right fluid channel 141 to provide a common cooling fluid return port. Outlet tube 16 returns cooling fluid 11 to the control console 51 from outlet manifold 132. Chinstrap 136 retains head-cooling cap 8 to the patient's head. Cooling module brackets 135 provides a secure means to mount cooling module 7 to the head-cooling cap 8, and to restrain cooling module umbilical 10 (FIGS. 1, 2, & 5). Ventricle-cooling catheter opening 14 provides surgical access to the part of the head where ventriculostomy is performed to place one or two ventricle-cooling catheter(s) (2 or 20) into lateral ventricle(s).

FIG. 14 depicts in planar form the path of left cooling fluid channel 140, and the path of right fluid cooling channel 141 through head-cooling cap 8. Also shown is flow control valve 131, inlet manifold 130, return manifold 132, cooling module retaining bracket 135, and ventricle-cooling catheter opening 14.

FIG. 15 depicts the construction of cooling fluid channels 140 & 141, the operation of fluid control valve 131 and inlet manifold 130, and mounting of inlet manifold 130 to outer liner 128. Fluid channel 140 and 141 are formed from outer liner 128, and inner liner 129 as shown using either adhesive 143, or thermal bonding. Inlet manifold 130 is attached to outer liner 128 with a compression grommet 142 as shown. Fluid control valve rotates within inlet manifold to: direct cooling fluid 11 flow to both fluid channels 140 and 141 (position shown), to direct cooling fluid 11 to cooling fluid channel 140 only (fluid control valve 131 rotated 90 degrees clockwise from position shown), to direct cooling fluid 11 to cooling fluid channel 141 (fluid control valve 131 rotated 90 degrees counterclockwise from position shown), or to prevent cooling fluid 11 from entering either cooling fluid channel 140 or 141 (fluid control valve 131 rotated 180 degrees from position shown).

Alternate Embodiments

Cooling of the brain may be accomplished by withdrawing cerebrospinal fluid from one or more ventricles, cooling the cerebrospinal fluid ex vivo and reintroducing the cooled cerebrospinal fluid back in the ventricle in a continuous or cyclical cycle. A compressor based refrigeration system may be used to cool the cooling fluid. A separate portable battery operated cooling unit may be provided for use with the head-cooling cap so that the head-cooling cap may be applied by emergency medical personnel in the field, and ventricle-cooling catheter(s) may be applied when the patient reaches the emergency room. A thermally conductive gel or other medium may be applied to the patient's hair to provide efficient cooling of the scalp by the head-cooling cap thereby eliminating the need to shave the patient's head. The CSF pump mechanism may be a mechanically driven rotary pump. Heat may be removed from the cooling block in the cooling module by a cooling mechanism other than thermoelectric heat pumps.

ADVANTAGES

From the description above there are a number of advantages my method and apparatus for inducing selective cerebral hypothermia for the prevention of secondary brain injury provide:

(a) The therapeutic agent (hypothermia) for preventing secondary injury according to this invention is applied directly to the brain.

(b) The therapeutic agent (hypothermia) for preventing secondary injury according to this invention is limited to the brain.

(c) Lower hypothermic temperatures can be practically achieved in the brain than can be achieved by the methods currently described in the art since only the brain is exposed to hypothermia.

(d) Hypothermic temperatures can be maintained longer in the brain than with methods described in the art.

(e) Cerebral hypothermia therapy may be applied faster than with methods described in the art since only the brain is cooled.

(f) Cerebral hypothermia therapy may be applied faster than with methods described in the art since head-surface cooling may be initiated in the field, and ventricle cooling may be initiated as soon as the patient reaches the emergency room.

(g) Selective cerebral hypothermia may be achieved without clinically significant temperature gradients within the brain.

(h) The degree of hypothermia in the brain can be adjusted according to the physiological response to hypothermia.

(i) Core body temperature may be precisely maintained at normal during cerebral hypothermia.

(j) The thalamus, hypothalamus and medulla are not cooled to a level that suppresses the autonomic nervous system.

I claim:

1. A method of inducing and maintaining selective cerebral hypothermia in a patient, comprising the steps of:
    (a) placing the distal end of at least one ventricle-cooling catheter into a lateral ventricle of the brain of said patient;
    (b) placing a head-cooling cap on the head of said patient; and
    (c) activating said ventricle-cooling catheter and said head-cooling cap whereby said brain is cooled by said ventricle-cooling catheter and by said head-cooling cap to a temperature lower than a body temperature of the patient.

2. The method of claim 1 further comprising:
    attaching a body-heating device to the body of said patient; and
    warming said body with said body-heating device while cooling the brain of the patient.

3. The method of claim 1 wherein said ventricle-cooling catheter comprises a temperature sensor.

4. The method of claim 1 wherein said ventricle-cooling catheter comprises a pressure sensor.

5. The method of claim 2 wherein said ventricle-cooling catheter comprises a means to remove fluid from, and insert fluid into, said lateral ventricle.

6. The method of claim 1 wherein said head-cooling cap comprises a means for selecting at least a portion of the scalp of said head for cooling by said head-cooling cap.

7. The method of claim 2 wherein said body-heating device is chosen from the group consisting essentially of a body-heating blanket, a body-heating garment, a body-heating catheter, or a body-heating source of light.

8. A brain cooling assembly comprising:
    a cooling catheter assembly having:
        a catheter defining a lumen, the catheter having a distal end and a proximal end, the distal end configured to insert within a brain ventricle of a body, and
        a cooling assembly coupled with the proximal end of the catheter, the cooling assembly having:
            a pump in fluid communication with the lumen defined by the catheter, the pump configured to remove fluid from the ventricle of the brain and return the fluid to the ventricle of the brain via the lumen defined by the catheter, and a heat transfer assembly in thermal communication with the pump and in fluid communication with the catheter, the heat transfer assembly configured to reduce a temperature of the fluid removed from the ventricle of the brain by the pump; and a body cooling device configured to cover an external surface of a head of the brain and configured to cool a portion of the brain oriented in proximity to the body cooling device.

9. The brain cooling assembly of claim 8 wherein the body cooling device comprises a cooling cap defining a first fluid channel and a second fluid channel, the first fluid channel configured to cool a first portion of the brain oriented in proximity to the first fluid channel and the second cooling channel configured to cool a second portion of the brain oriented in proximity to the second fluid channel.

10. The brain cooling assembly of claim 8 wherein the catheter comprises a temperature sensor configured to orient in thermal communication with the fluid of the ventricle.

11. The brain cooling assembly of claim 8 wherein the catheter comprises a pressure sensor oriented on the distal end of the catheter.

12. The brain cooling assembly of claim 8 further comprising a drainage assembly in fluid communication with the lumen defined by the catheter.

13. The brain cooling assembly of claim 8 wherein the lumen defined by the catheter comprises an aspiration channel defining an aspiration port and an infusion channel defining an infusion port, the aspiration port configured to orient within an anterior horn of the brain ventricle and the infusion port configured to orient within an inferior horn of the ventricle.

14. The brain cooling assembly of claim 8 wherein the brain cooling system further comprises a body heating device configured to increase the temperature of the body.

15. The brain cooling assembly of claim 8 wherein the body heating device comprises a warming catheter configured to insert within a vena cava of the body.

16. The brain cooling assembly of claim 8 wherein the heat transfer assembly defines a circuitous fluid path.

17. A brain cooling system comprising:
a cooling catheter assembly having:
a catheter defining a lumen, the catheter having a distal end and a proximal end, the distal end configured to insert within a brain ventricle of a body, and
a cooling assembly coupled with the proximal end of the catheter, the cooling assembly having:
a pump in fluid communication with the lumen defined by the catheter, the pump configured to remove fluid from the ventricle of the brain and return the fluid to the ventricle of the brain via the lumen defined by the catheter, and
a heat transfer assembly in thermal communication with the pump and in fluid communication with the catheter, the heat transfer assembly configured to reduce a temperature of the fluid removed from the ventricle of the brain by the pump;
a body cooling device configured to cover an external surface of a head of the brain and configured to cool a portion of the brain oriented in proximity to the body cooling device; and
a control console in thermal communication with the cooling catheter assembly and the body cooling device, the control console configured:

(i) to provide cooling fluid to the heat transfer assembly, and
(ii) to provide cooling fluid to the body cooling device.

18. The brain cooling system of claim 17 further comprising a body heating device in thermal communication with the control console, the body heating device configured to increase the temperature of the body.

19. A method for adjusting a degree of cerebral hypothermia of a brain comprising:
covering an external surface of a head with a head-cooling device configured to remove heat from the external surface of the head;
providing selective cerebral hypothermia to the brain by cooling a portion of the brain oriented in proximity to the head-cooling device;
measuring an intra-cranial pressure of the head associated with the brain;
detecting a change in the intra-cranial pressure; and
altering the degree of cerebral hypothermia of the brain in response to detecting the change in intra-cranial pressure.

20. The method of claim 19 wherein measuring the intra-cranial pressure of the head associated with the brain comprises measuring a pressure within a lateral ventricle of the brain.

21. The method of claim 19 wherein:
detecting a change in the intra-cranial pressure comprises detecting an increase in the intra-cranial pressure; and
altering the degree of cerebral hypothermia of the brain comprises increasing a level of cerebral hypothermia in response to detecting the increase in intra-cranial pressure.

22. A system for inducing cerebral hypothermia comprising:
a head cooling cap configured to cool a region of a surface of a head to a level that induces cerebral hypothermia;
a brain probe having a sensor configured to detect at least one physiological parameter of a brain; and
a control console in thermal communication with the head-cooling cap and in electrical communication with the sensor of the brain probe, the control console configured to adjust cooling by the head-cooling cap in response to a signal received from the sensor of the brain probe.

23. The system of claim 1 wherein the brain probe is configured to insert within the brain.

24. The system of claim 1 wherein the head-cooling cap defines an opening configured to allow insertion of the probe into the brain of the patient at a location relative to landmarks of the head while the head cooling cap is mounted on the head.

25. The system of claim 22 further comprising a warming device in thermal communication with the console.

26. The system of claim 22 wherein the control console is configured to adjust cooling by the head-cooling cap in response to a pressure signal received from the sensor of the brain probe, the pressure signal indicative of brain pressure.

27. The system of claim 22 wherein the control console is configured to adjust cooling by the head-cooling cap in response to a temperature signal received from the sensor of the brain probe, the temperature signal indicative of brain temperature.

28. The system of claim 22 wherein the control console is configured to circulate fluid through the head-cooling cap.

29. The system of claim 28 wherein the control console comprises a cooling assembly configured to cool the fluid.

30. The system in claim 23 wherein said probe comprises a ventricle cooling catheter.

31. A method for controlling cerebral hypothermia comprising:
   placing a head-cooling cap on a patient's head;
   placing a brain probe into the patient's brain, the brain probe having a sensor configured to detect at least one physiological parameter of a brain;
   cooling cap in thermal communication with the console and the sensor of the brain probe in electrical communication with the console; and
   activating the control console to (i) receive a signal from the sensor of the brain probe and (ii) adjust cooling by the head-cooling cap in response to the signal received from the sensor of the brain probe.

32. The method of claim 31 wherein the step of placing a brain probe into the patient's brain comprises placing a ventricle cooling catheter into the patient's brain.

33. The method of claim 31 wherein the step of activating the control console further comprises the steps of:
   cooling a fluid; and
   circulating the fluid through the head-cooling cap.

34. The method of claim 31 wherein when receiving a signal from the sensor of the brain probe, the control console receives a brain pressure signal from the sensor of the brain probe.

35. The method of claim 31 wherein when receiving a signal from the sensor of the brain probe, the control console receives a brain temperature signal from the sensor of the brain probe.

36. The method of claim 31 wherein:
   receiving a signal from the sensor of the brain probe further comprises detecting an increase in the intra-cranial pressure based upon the signal; and
   adjusting cooling by the head-cooling cap in response to the signal received from the sensor of the brain probe comprises increasing a level of cerebral hypothermia in response to detecting the increase in intra-cranial pressure based upon the signal.

37. A head-cooling device comprising:

a cap defining a plurality of cooling zones;

a fluid inlet coupled to the cap and in fluid communication with the cooling zones the fluid inlet configured to couple to a cooling fluid source; and a valve in fluid communication with the fluid inlet, the valve configured to direct flow of cooling fluid from the cooling fluid source to at least one of the plurality of cooling zones to cool a portion of a head oriented in proximity to the at least one of the plurality of cooling zones.

38. The body cooling device of claim 37 wherein the plurality of cooling zones comprises a first hemispherical cooling zone and a second hemispherical cooling zone.

39. The body cooling device of claim 38 wherein the cap further defines a first fluid channel associated with the first hemispherical cooling zone and a second fluid channel associated with the second hemispherical cooling zone, the first fluid channel configured to cool a first portion of a head oriented in proximity to the first fluid channel and the second cooling channel configured to cool a second portion of the brain oriented in proximity to the second fluid channel.

* * * * *

UNITED STATES PATENT AND TRADEMARK OFFICE
CERTIFICATE OF CORRECTION

PATENT NO. : 7,156,867 B2
APPLICATION NO. : 10/330638
DATED : January 2, 2007
INVENTOR(S) : Charles D. Lennox It is certified that error appears in the above-identified patent and that said Letters Patent is hereby corrected as shown below:

In the Claims:

Column 18, line 46, in claim 23 (previously prosecuted as claim 37), change the dependent claim from "claim 1" to --claim 22--.

Column 18, line 48, in claim 24 (previously prosecuted as claim 38), change the dependent claim from "claim 1" to --claim 22--.

Column 19, line 5, in claim 31 (previously prosecuted as claim 45), after "head" add, --the head-cooling cap in thermal communication with a control console--.

Column 19, line 8, in claim 31 (previously prosecuted as claim 45), after "brain" add, --the sensor in electrical communication with the control console; and--.

Column 19, lines 9-11, in claim 31 (previously prosecuted as claim 45), delete "cooling cap in thermal communication with the console and the sensor of the brain probe in electrical communication with the console; and".

Column 20, line 14, in claim 37 (previously prosecuted as claim 51), change "configured to" to --capable of--.

Column 20, line 14, in claim 37 (previously prosecuted as claim 51), change "direct" to --directing--.

Column 20, line 15, in claim 37 (previously prosecuted as claim 51), change "at least one" to --fewer than all--.

Column 20, line 17, in claim 37 (previously prosecuted as claim 51), change "at least one" to --fewer than all--.

Column 20, line 19, In claim 38 (previously prosecuted as claim 52), change "body cooling" to --head-cooling--.

UNITED STATES PATENT AND TRADEMARK OFFICE
CERTIFICATE OF CORRECTION

PATENT NO. : 7,156,867 B2
APPLICATION NO. : 10/330638
DATED : January 2, 2007
INVENTOR(S) : Charles D. Lennox It is certified that error appears in the above-identified patent and that said Letters Patent is hereby corrected as shown below:

Column 20, line 22, in claim 39 (previously prosecuted as claim 53), change "body cooling" to --head-cooling--.

Signed and Sealed this

First Day of May, 2007

JON W. DUDAS
*Director of the United States Patent and Trademark Office*